(12) United States Patent
Zuckerman-Stark et al.

(10) Patent No.: US 11,259,708 B2
(45) Date of Patent: Mar. 1, 2022

(54) SYSTEM AND METHOD FOR PAIN MONITORING USING A MULTIDIMENSIONAL ANALYSIS OF PHYSIOLOGICAL SIGNALS

(71) Applicant: Medasense Biometrics Ltd., Ramat Gan (IL)

(72) Inventors: Galit Zuckerman-Stark, Tel Aviv (IL); Mark Kliger, Beer-Sheba (IL)

(73) Assignee: Medasense Biometrics Ltd., Ramat Gan (IL)

( * ) Notice: Subject to any disclaimer, the term of this patent is extended or adjusted under 35 U.S.C. 154(b) by 0 days.

(21) Appl. No.: 16/983,466

(22) Filed: Aug. 3, 2020

(65) Prior Publication Data
US 2020/0359914 A1 Nov. 19, 2020

Related U.S. Application Data

(63) Continuation of application No. 15/349,098, filed on Nov. 11, 2016, now Pat. No. 10,743,778, which is a
(Continued)

(51) Int. Cl.
*A61B 5/0205* (2006.01)
*G16H 50/20* (2018.01)
(Continued)

(52) U.S. Cl.
CPC .......... *A61B 5/02055* (2013.01); *A61B 3/112* (2013.01); *A61B 5/02* (2013.01); *A61B 5/0261* (2013.01); *A61B 5/0295* (2013.01); *A61B 5/24* (2021.01); *A61B 5/318* (2021.01); *A61B 5/369* (2021.01); *A61B 5/392* (2021.01); *A61B 5/398* (2021.01); *A61B 5/4821* (2013.01); *A61B 5/4824* (2013.01); *A61B 5/7203* (2013.01); *A61B 5/726* (2013.01); *A61B 5/7264* (2013.01); *A61B 5/7267* (2013.01); *A61B 5/7275* (2013.01); *A61B 5/7282* (2013.01); *G06N 20/00* (2019.01); *G16H 40/63* (2018.01); *G16H 50/20* (2018.01); *G16H 50/30* (2018.01); *G16H 50/70* (2018.01); *A61B 5/021* (2013.01);
(Continued)

(58) Field of Classification Search
None
See application file for complete search history.

(56) References Cited

U.S. PATENT DOCUMENTS 6,117,075 A 9/2000 Barnea
6,571,124 B1 5/2003 Storm
(Continued)

FOREIGN PATENT DOCUMENTS

EP 1495715 1/2005
EP 1704817 9/2006
(Continued)

OTHER PUBLICATIONS

Akselrod et al., (1981) Power spectrum analysis of heart rate fluctuation a quantitative probe of beat-to-beat cardiovascular control, Science 213(4504): 220-222.
(Continued)

*Primary Examiner* — Brian T Gedeon
(74) *Attorney, Agent, or Firm* — Greenberg Traurig, LLP

(57) ABSTRACT

The present invention is for a method and system for pain classification and monitoring optionally in a subject that is an awake, semi-awake or sedated.

1 Claim, 9 Drawing Sheets

Related U.S. Application Data continuation of application No. 13/945,657, filed on Jul. 18, 2013, now Pat. No. 9,498,138, which is a continuation of application No. 12/779,963, filed on May 14, 2010, now Pat. No. 8,512,240, which is a continuation-in-part of application No. PCT/IL2008/001493, filed on Nov. 13, 2008.

(60) Provisional application No. 61/180,161, filed on May 21, 2009, provisional application No. 60/987,782, filed on Nov. 14, 2007.

(51) Int. Cl.

| | |
|---|---|
| A61B 5/00 | (2006.01) |
| A61B 5/021 | (2006.01) |
| A61B 5/024 | (2006.01) |
| G16H 50/30 | (2018.01) |
| G16H 50/70 | (2018.01) |
| G06N 20/00 | (2019.01) |
| A61B 5/02 | (2006.01) |
| A61B 5/24 | (2021.01) |
| A61B 5/318 | (2021.01) |
| A61B 5/369 | (2021.01) |
| A61B 5/392 | (2021.01) |
| A61B 5/398 | (2021.01) |
| G16H 40/63 | (2018.01) |
| A61B 3/11 | (2006.01) |
| A61B 5/026 | (2006.01) |
| A61B 5/0295 | (2006.01) |
| A61B 5/0533 | (2021.01) |
| A61B 5/083 | (2006.01) |

(52) U.S. Cl.
CPC ....... *A61B 5/02405* (2013.01); *A61B 5/02416* (2013.01); *A61B 5/0533* (2013.01); *A61B 5/0836* (2013.01); *A61B 2562/0219* (2013.01)

(56) References Cited

U.S. PATENT DOCUMENTS

| | | | |
|---|---|---|---|
| 6,685,649 | B2 | 2/2004 | Korhonen |
| 6,757,558 | B2 | 6/2004 | Lange |
| 7,215,994 | B2 | 5/2007 | Huiku |
| 7,367,949 | B2 | 5/2008 | Korhonen |
| 7,407,485 | B2 | 8/2008 | Huiku |
| 7,463,927 | B1 | 12/2008 | Chaouat |
| 7,553,286 | B2 | 6/2009 | Huiku |
| 7,610,086 | B1 | 10/2009 | Ke et al. |
| 7,783,114 | B2 | 8/2010 | Bradski |
| 7,873,479 | B2 | 1/2011 | Lois et al. |
| 7,908,091 | B2 | 3/2011 | Harvey et al. |
| 2002/0123670 | A1 | 9/2002 | Goetzke |
| 2003/0166996 | A1 | 9/2003 | Kim |
| 2004/0117212 | A1 | 6/2004 | Kong |
| 2005/0010116 | A1 | 1/2005 | Korkonen |
| 2005/0272984 | A1 | 12/2005 | Huiku |
| 2006/0052720 | A1 | 3/2006 | Ross |
| 2006/0217614 | A1 | 9/2006 | Takala |
| 2006/0217615 | A1 | 9/2006 | Huiku |
| 2006/0217628 | A1 | 9/2006 | Huiku |
| 2007/0010723 | A1 | 1/2007 | Uutela |
| 2007/0213783 | A1 | 9/2007 | Pless |
| 2007/0219433 | A1 | 9/2007 | Stupp |
| 2008/0086272 | A1 | 4/2008 | Fillet |
| 2008/0242955 | A1 | 10/2008 | Uutela |
| 2008/0288227 | A1 | 11/2008 | Higgins |
| 2010/0212666 | A1 | 8/2010 | Bouillon |
| 2011/0040713 | A1 | 2/2011 | Colman |

FOREIGN PATENT DOCUMENTS

| | | |
|---|---|---|
| EP | 1704819 | 9/2006 |
| WO | 20090033181 | 3/2009 |

OTHER PUBLICATIONS

Belkin (2003) Laplacian eigenmaps for dimensionality reduction and data representation. Neural Computation 15(6): 1373-1396.
Bishop (2006) Pattern recognition and machine learning, Springer, New York, NY, USA.
Borg and Groenen (2005) Modern Multidimensional Scaling: theory and applications, Springer-Verlag, New York, USA.
Breiman (1984) Classification and Regression Trees, Wadsworth, Belmont, CA, USA.
Breiman (1996) Bagging Predictors. Machine Learning 24(2): 123-140.
Breiman (2001) Random Forests. Machine Learning 45(1): 5-32.
Bruhn et al., (2000) Approximate entropy as an electroencephalographic measure of anesthetic drug effect during desoflurane anesthesia. Anesthesiology, 92(3): 715-772.
Chapelle et al., (2002) Choosing Multiple Parameters for Support Vector Machines. Machine Learning 46: 131-159.
Coifman et al., (2005) Geometric diffusions as a tool for harmonic analysis and structure definition of data. Proc Natl Acad Sci USA 102(21) 7426-7438.
D'aspermont et al., (2005) A direct formulation for sparse PCA using semidefinite programming, in Advances in Neural Information Processing Systems (NIPS), MIT Press, Cambridge, MA, USA.
Deschamps et al., (2004) Autonomic nervous system response to epidural analgesia in laboring patients by wavelet transform of heart rate and blood pressure variability. Anesthesiology 101(1): 21-27.
Donoho and Grimes (2003) Hessian eigenmaps: Locally linear embedding techniques for high-dimensional data. Proc Natl Acad Sci USA 100(1): 5591-5596.
Duda et al., (2000) Pattern Classification, Willey, New York, NY,USA.
GE brochure as described in EMEA (M119389/1109).
Goncharova and Barlow (1990) Changes in EEG mean frequency and spectral purity during spontaneous alpha blocking. Electroencephalogr Clin Neurophysiol 76(3): 197-204.
Gronwall and Wrightson (1974) Delayed Recovery of intellectual function after minor head injury. Lancet 304: 605-609.
Guignard (2006) Monitoring analgesia: Best practice and research. Clinical anaesthesiology 20(1): 161-180.
Guo et al., (2007) Regularized linear discriminant analysis and its application in microarrays. Biostatistics 8(1): 86-100.
Hastie (2008) The elements of statistical learning. Data mining, inference, and prediction, Springer, New York, NY, pp. 306,595.
Hastie (2009) Tile elements of statistical learning: data mining, inference, and prediction, Springer, New York, NY, USA, pp. 306, 350-351, 595.
Hjorth (1973) The physical significance of time domain descriptors in EEG analysis. Electroencephalogr Clin Neurophysiol 34(3): 321-325.
Huiku et al., (2007) Assessment of surgical stress during general anaesthesia. Br J Anaesth 98(4) 447-455.
Kohavi and Jogn (1997) Wrappers for Feature Subset Selection. Artificial intelligence 97(1-2): 273-324.
Lidberg and Wallin (1981) Sympathetic Skin Nerve Discharges in Relation to Amplitude of Skin Resistance Responses. Psychophysiology 18(3): 268-270.
Loggia and Napadow (2012) Multi-parameter autonomic-based pain assessment more is more? Pain 153(9): 1779-1780.
Malik (1996) Heart rate variability: standards of measurement, physiologicai interpretation and clinical use. Task Force of the European Society of Cardiology and the North American Society of Pacing and Electrophysiology Eur Heart J 17(3): 354-381.
Moghaddam et al., (2006) Generalized Spectral Bounds for Sparse LOA, Proceedings of International Conference of Machine Learning (ICML), pp. 641-648.

(56) References Cited

OTHER PUBLICATIONS

Moghaddam et al., (2006) Spectra! Bounds for Sparse PCA: Exact and Greedy Algorithms, in Advances in Neural Information Processing Systems (NIPS), pp. 915-922, MIT Press, Cambridge, MA, USA.

Oppenheim (1999) Discrete-time signal Processing, Prentice Hail, Upper Saddle River, NJ, USA.

Pagani et al., (1992) Low-frequency components of cardiovascular variabilities as markers of sympathetic modulation. Trends in pharmacological sciences 13(2): 50-54.

Pan and Tompkins (1985) A real-time QRS detection algorithm, IEEE Transactions Biomedical Engineering 32(3): 230-236.

Pop-Jordanova and Pop-Jordanov (2005) Spectrum-weighted EEG frequency ("brain-rate") as a quantitative indicator of mental arousal. Prilozi Makedonska akademija na naukite i umetnostite, Oddelenie za biolovski i medicinski nauki 26(2) 35-42.

Rangayyan (2002) Biomedical signal analysis: A case study approach. IEEE Press, John Wiley & Sons, New York, NY, USA.

Roweiss and Saul (2000) Nonlinear dimensionality reduction by locally linear embedding. Science 290:2323-2326.

Sanei and Chambers (2007) EEG signal processing, John Wiley & Sons, New York, NY, USA.

Schlogl (2006) A comparison of multivariate autoregressive estimators. Signal Processing 86(9): 2426-2429.

Scholkopf et al., (1998) Nonlinear component analysis as a kernel eigenvalue problem. Neural Cornput 10(5): 1299-1319.

Seitsonen et al., (2005) EEG spectral entropy, heart rate, photoplethysmography and motor responses to skin incision during sevoflurane anaesthesia. Acta Anaesthesiol Scand 49: 284-292.

Tenenbaum et al., (2000) A global geometric framework for nonlinear dimensionality reduction. Science 290: 2319-2323.

Thomas and Evans (1989) Lower oesophageal contractility monitoring during anaesthesia for cardiac surgery: preliminary observations. Ann R Coll Surg Engl 71(5): 311-315.

Tibshirani et al., (2002) Diagnosis of multiple cancer types by shrunken centroids of gene expression. Proc Natl Acad Sci USA 99(10): 6567-6572.

Treister et al., (2012) Differentiating between heat pain intensities: the combined effect of multiple autonomic parameters. Pain153(9): 1807-1814.

Van Den Berg et al., (2006) Attenuation of the haemodynamic responses to noxious stimuli in patients undergoing cataract surgery. A comparison of magnesium sulphate, esmolol, lignocaine, nitroglycerine and placebo given i.v. with induction of anaesthesia. Eur J Anaesthesiol 14(2): 134-147.

Vapnik (1998) Statistical Learning Theory, Wiley, New York, NY, USA.

Wackermann (1999) Towards a quantitative characterisation of functional states of the brain: from the non-linear methodology to the global linear description. Int J Psycl1ophysiol 34(1): 65-80.

Weiss et al., (1980) Pulse transit time in the analysis of autonomic nervous system effects on the cardiovascular system. Psychophysiology 17(2): 202-207.

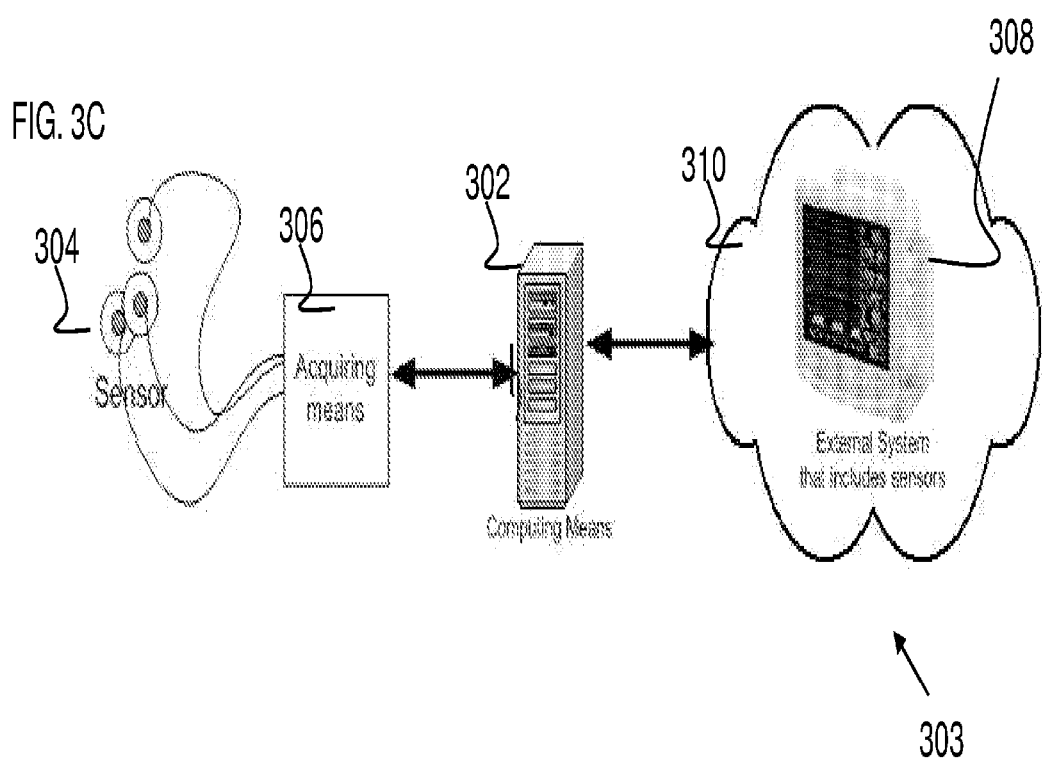

SYSTEM AND METHOD FOR PAIN MONITORING USING A MULTIDIMENSIONAL ANALYSIS OF PHYSIOLOGICAL SIGNALS

CROSS-REFERENCE TO RELATED APPLICATIONS

This application is a Continuation of U.S. application Ser. No. 15/349,098, filed Nov. 11, 2016, which is a Continuation of U.S. application Ser. No. 13/945,657, filed Jul. 18, 2013, which is a Continuation of U.S. application Ser. No. 12/779,963, filed May 14, 2010, which claims the benefit of U.S. Provisional Application Serial No. 61/180,161, filed on May 21, 2009 and is Continuation-in-Part of PCT International Application No. PCT/IL2008/001493, filed on Nov. 13, 2008, which claims the benefit of U.S. Provisional Application Serial No. 60/987,782, filed on Nov. 14, 2007, all of which are hereby incorporated by reference in their entireties.

FIELD OF THE INVENTION

The present invention relates to a system and a method for pain monitoring by performing a multidimensional analysis of a plurality of physiological signals, and in particular, to such a system and method in which pain monitoring, classification and identification is established for individuals exhibiting various states of consciousness.

BACKGROUND OF THE INVENTION

Pain is an unpleasant sensory and emotional experience associated with actual or potential tissue damage, or described in terms of such damage. The inability to communicate verbally does not negate the possibility that an individual is experiencing pain and is in need of appropriate pain-relieving treatment (www.iasp-pain.org/AM/). Pain is always subjective where each individual learns the application of the word through experiences related to injury in early life. Biologists recognize that those stimuli which cause pain are liable to damage tissue. Accordingly, pain is that experience we associate with actual or potential tissue damage. It is unquestionably a sensation in a part or parts of the body, but it is also always unpleasant and therefore also an emotional experience. Experiences which resemble pain but are not unpleasant, e.g., pricking, should not be called pain.

"Pain Threshold" is defined as the least experience of pain which a subject can recognize as pain. Traditionally, this threshold has been defined as the least stimulus intensity at which a subject perceives pain. Properly defined, however, the threshold should be related to the experience of the patient, whereas the measured intensity of the stimulus is an external event. Because the threshold stimulus can be recognized as such and measured objectively, it has been common usage for most pain research workers to define the threshold in terms of the stimulus, even though it is preferable to avoid such a definition. In psychophysics, a threshold is defined as the level at which 50% of stimuli are recognized. Thus, the pain threshold would be the level at which 50% of stimuli would be recognized as painful. As the stimulus is only one aspect of pain, it cannot be a measure or a definition of pain.

"Pain Tolerance Level" is defined as the greatest level of pain which a subject is prepared to tolerate. As with pain threshold, the pain tolerance level is the subjective experience of the individual. The stimuli which are normally measured in relation to its production are the pain tolerance level stimuli and not, the level itself. Thus, the same argument applies to pain tolerance level as to pain threshold, and it should not be defined in terms of the external stimulation as such.

Pain may be described as either a symptom or an indication of an underlying problem. However pain in and of itself may be a considered a diagnosis or condition. Fibromyalgia is an example of a condition wherein pain is not a symptom but rather a finding. Many such diagnosis are becoming more prevalent as pain gains recognition for being a condition and not merely a symptom that may be subsided once the underlying problem is treated.

However, to date state of the art pain monitoring has primarily manifested and centered on individual in the unconscious state, in providing a Depth of Anesthesia (herein referred to as DOA) reading and/or monitoring.

Depth of Anesthesia monitoring (herein after referred to as DOA or DOA Monitoring) uses physiological signals that represent certain autonomic nervous system activity or brain activity for monitoring a certain state of a patient under anesthesia. DOA monitoring is a general term for pain and/or awareness and/or muscle activity monitoring when a patient is under general anesthesia. In the unconscious anesthetized state pain and awareness are difficult to be distinguished as they both may result in the same physiological symptoms.

Conversely, pain monitoring attempts to detect sensation of physical discomfort and is not limited to the state of consciousness of a subject. Therefore during pain monitoring a patient can be and is often fully awake.

Although DOA monitoring has gained in popularity over the last decade primarily because of the increase in the number of publication relating to "awareness during anesthesia", it is only in the last few years, that pain monitoring has become a subject to increased awareness.

State of the art DOA and/or pain monitors are described in U.S. Pat. No. 6,117,075 to Barnea, U.S. Pat. No. 6,571,124 to Storm, US Patent Publication No. 2006/0217615 to Huiku, U.S. Pat. No. 6,757,558 to Lange, etc. each describing the independent use of a physiological signals such as skin conductance, EEG, ECG, PPG, temperature etc., to determine the DOA or pain level. However, medical studies have shown that a usage of combination of parameters from different physiological signals significantly improved the pain and no-pain classification performance achieved compared with discrimination using any single signal alone (Guignard 2006), Other state of the art DOA monitors, such as those described by U.S. Pat. Nos. 6,685,649 and 7,367,949 and European Patent No. EP1495715 to Korhonen describe a DOA monitoring system for a user that is under sedation or anesthesia. These publications are centered and rely upon analysis of a single parameter associated with the cardiovascular system, specifically using blood pressure (BP), heart rate variability are correlated to the detection of pain.

U.S. Pat. No. 7,215,994 to Huiku discloses a method for monitoring a state of anesthesia or sedation by comparing cortex related EEG biopotential signal data from the patient to subcortex-related biosignal data from the patient, the subcortex-related biosignal data including at least bioimpedance signal data. However although a few signals are used together to obtain a DOA reading this system is limited to individuals that are fully sedated and therefore unconscious.

A state of the art pain monitoring system is described in U.S. Pat. No. 7,407,485 to Huiki, that presents a pain monitoring system that is based on one or more physiological parameter that are measured, normalized and then compared to 'a threshold surface', while the frequency of threshold crossing infers the relative pain level experienced.

Other prior art publications such as US 2006/0217614 to Takala et al, US 2006/0217615 to Huiki et al, US 2006/0217628 Huiki, and in US 2007/0010723 Uutela et al, report the use of a group of physiological features to form an Index of Nociception to determine the state of a patient.

Prior art teaches DOA systems that are associated with a few physiological signals and parameters to infer the pain state of a patient while under sedation. Similarly prior art teaches pain monitoring systems that are limited in that the system is heavily dependent on the number of physiological variables used to obtain appropriate pain indication.

SUMMARY OF THE INVENTION

The present invention overcomes these deficiencies of the background by providing a system and method for pain monitoring, for pain experienced in various states of consciousness that optionally and preferably takes into account a plurality of physiological signals and parameters to determine the pain level.

Within the context of the present application the following terms are used as is understood and known by those skilled in the art.

States of consciousness within the context of the present application the terms states of consciousness optionally includes sedated, partially sedate and awake.

Within the context of the present invention the following terms and corresponding shorthand are interchangeably used throughout the text for the following terms as is understood and known by those skilled in the art. Standard deviation ('std'), Very Low Frequency ("VLF"), Low Frequency ("LF"), High Frequency ("HF").

Within the context of the present invention the term Galvanic Skin Response (herein referred to as GSR) may also be referred to as Electro Dermal Response (EDR) or Skin Conductance Response (SCR), commonly refers to methods for measuring the electrical resistance of the skin and measured, optionally this is measured with two or three surface electrodes and acquiring a base measure.

Within the context of the present invention the term Electro-Gastro-Gram (herein referred to as EGG) is a non-invasive method for the measurement of gastric myoelectrical activity using abdominal surface electrodes.

Within the context of the present invention the term Pupil Diameter Measurement (herein referred to as PD) measures pupil size and movement. Optionally PD may be measured by infrared videography or computerized pupillometry.

Within the context of the present invention the term Electromyography (herein referred to as EMG), refers to a technique for recording and evaluating physiologic properties of muscle activity either at rest or while contracting. EMG signals are optionally and preferably recorded with surface electrodes. Optionally and preferably a plurality of location specific EMG signals may be recorded from various locations on a subject and/or muscle groups. For example Frontalis (scalp) Electromyogram (herein referred to as FEMG) measures over the frontalis muscle underlying the forehead.

Within the context of the present invention the term PhotoPlethysmoGraph (herein referred to as PPG) is a non-invasive transducer to measure the relative changes of blood volume from a finger.

Within the context of the present invention the term Electro-Cardio-Gram (herein referred to as ECG) is a graphic representation of an electrocardiograph, which records the electrical activity of the heart.

Within the context of the present invention the term ElectroEncephaloGraph (herein referred to as EEG) is the measurement of electrical activity produced by the brain as recorded from electrodes placed on the scalp.

Within the context of the present invention the term ElectroOculaGraph (herein referred to as EOG) is the measurement of electrical activity produced by the eye movement and retina as recorded from electrodes placed on the face and frontal lobe.

Within the context of the present invention the term Blood pressure (herein referred to as BP), refers to a signal capture an arterial blood pressure, i.e., to the force exerted by circulating blood on the walls of the larger arteries. Optionally BP may be measured by invasive or non-invasive methods.

Within the context of the present invention the term Laser Doppler Velocimetry (herein referred to as LDV) quantifies blood flow in tissues for example such as skin to extract different features such as the vasomotor reflex (SVMR).

Within the context of the present invention the term Capnograph refers to a device provided to monitor the concentration or partial pressure of carbon dioxide (CO2) in the respiratory gases in this context it is also used for any measurement of concentration end-tidal Nitrous oxide (N2O), oxygen (O2), or Anesthetic Agent.

Within the context of the present invention the term Accelerometer is a device for measuring acceleration and gravity induced reaction forces.

Within the context of the present invention the term physiological signals refers to any measurable signal or event that is optionally measured directly or indirectly from a subject through sensors, transducers or the like preferably providing a measurement indicative of the state of a patient. Optionally and preferably the physiological signals may be further analyzed, processed, or otherwise manipulated to provide further details regarding the state of a patient. Physiological signals for example include but are not limited to, blood pressure, respiration, internal and/or surface temperature, pupil diameter, GSR, and signals received and/or abstracted and/or derived from ECG, PPG, EOG, EGG, EEG, EMG, EGG, LDV, capnograph and accelerometer or any portion or combination thereof. Preferably a physiological signal may further comprise any signal that is measureable and/or detectible from a subject.

Within the context of the present invention the term feature extraction commonly refers to the processes, manipulations and signal processing measures performed to analyze a physiological signal most preferably to abstract from the signal valuable information, data or subsignal reflective of the state of a patient, Within the context of the present invention the term feature referrers to at least one or more of physiological features, a priori features, a priori data, external data or external input. Optionally features may be quantitative or qualitative or the like.

Within the context of the present invention the term a priori data, a priori feature, external feature or data may be interchangeably used to refer to any data received or otherwise obtained about a subject for example including but not limited to nociception response, conceptual response, context relevance response, Behavioral response, subject history, gender, type of medicine, diagnostics, patient condition, patient definition of pain level, age group, weight, height, historical data, drug history, drug interaction or the like data. Most preferably, this inclusion of a priori data increases the classification efficiency of the optional classifiers used with the system and method of the present invention.

Within the context of this application the term physiological features preferably refers to features extracted from a physiological signal through feature extraction to ascertain data associated with a physiological signal. An exemplary list of features optionally utilized within the system and method of the present invention are depicted in Table 1, preferably a plurality of features may be used in any combination thereof.

TABLE 1 list of optional plurality of features

| # | Signal | Feature | Description | Number of features |
|---|--------|---------|-------------|--------------------|
| 1. | PPG | PPG Peak (P) and Trough (T) amplitude, mean amplitude and std of amplitude | The amplitude of the Peak (P) and the Trough (T) of the PPG signal, mean amplitudes and STD of amplitudes in predefined time window. Peak denotes a point of maximum blood volume in a finger; Trough denotes a minimum basal blood volume. | 6 |
| 2. | PPG | PPG Maximum Rate (MR) point | The amplitude of the maximum rate point (MR) of PPG signal, mean amplitude and STD of amplitude in predefined time window. Maximum rate is a point between onset injection and Peak where maximum rate of blood volume increase is observed. | 3 |
| 3. | PPG | PPG dicrotic notch | The amplitude of the dicrotic notch of PPG signal, mean amplitude and STD of amplitude in predefined time window. | 3 |
| 4. | PPG | PP/PT/PN/NT/NM intervals, mean and std (variability) of interval | The time interval between peak to peak, peak to trough, peak to notch, notch to trough, notch to maximum rate, in PPG signal, mean interval and STD (variability) of intervals in predefined time window. | 15 |
| 5. | PPG Freq. | P-P Variability (PPG-HRV) VLF, LF, MF and HF | Power of the Very Low Frequency (0.0033 Hz-0.04 Hz), Low Frequency (0.04 Hz-0.15 Hz), and High Frequency (0.15 Hz-0.4 Hz) frequency bands of power spectrum of the P-P interval (PPG based Pulse Rate Variability power spectrum) in predefined time window. | 3 |
| 6. | PPG Freq. | P-P Variability LF/HF | Ratio between LF (0.04 Hz-0.15 Hz) PPG-HRV power spectrum and HF (0.15 Hz-0.4 Hz) PPG-HRV power spectrum in predefined time window. | 1 |
| 7. | PPG | Area Under Curve (AUC) | The integral of single beat of PPG signal. | 1 |
| 8. | PPG | Spectrum PPG envelope | Power Spectrum of the envelope of PPG signal. Envelope—Peak-Trough of PPG signal. | 1 |
| 9. | PPG | PPG Variability wavelet analysis | Wavelet analysis of the P-P interval variability. | 1 |
| 10. | PPG Freq | PPG-RSA (Respiratory sinus arrhythmia) | The frequency of dominant peak at HF (0.15 Hz-0.4 Hz) band of PPG-HRV power spectrum in predefined time window. | 1 |
| 11. | GSR | GSR amplitude, mean amplitude and std of amplitude | The amplitude of the GSR signal, mean amplitude and STD of amplitude in predefined time window. | 2 |
| 12. | GSR | GSR Peak (P) amplitude, mean amplitude and std of amplitude | The amplitude of the Peak (P) of GSR signal, mean amplitude and STD of amplitude in predefined time window. | 1 |
| 13. | GSR | PP interval, mean and std (variability) of interval | The time interval between peak to peak of GSR signal, mean interval and STD (variability) of intervals in predefined time window. | 1 |

TABLE 1-continued list of optional plurality of features

| # | Signal | Feature | Description | Number of features |
|---|--------|---------|-------------|--------------------|
| 14. | GSR | Phasic EDA, amplitude, mean amplitude and std of amplitude | The amplitude of the first derivative of the GSR signal (EDA phasic), mean amplitude and STD of amplitude in predefined time window. | 1 |
| 15. | GSR | Spectrum of the GSR signal | Power Spectrum of the GSR signal in predefined time window. | 1 |
| 16. | GSR | Peak Amplitude | The amplitude of the highest peak of the power spectrum in predefined time window. | 1 |
| 17. | GSR | Peak Frequency | The frequency of the highest peak of the power spectrum in predefined time window. | 1 |
| 18. | GSR | GSR wavelet analysis | Wavelet analysis of the interval. | 1 |
| 19. | ECG | Q/R/S/T/P amplitude, mean and std of amplitude | The amplitude of the Q/R/S/T/P pulse, mean amplitude and STD of amplitude in predefined time window. | 15 |
| 20. | ECG | RR/PQ/PR/QT/RS/ST interval, mean and std (variability) of interval | The interval between each pulse or between internal pulse waves RR/PQ/PR/QT/RS, mean interval and STD (variability) of intervals in predefined time window. | 15 |
| 21. | ECG Freq. | R-R Variability (ECG-HRV) VLF, LF, MF and HF | Power of the Very Low Frequency (0.0033 Hz-0.04 Hz), Low Frequency (0.04 Hz-0.15 Hz), and High Frequency (0.15 Hz-0.4 Hz) frequency bands of power spectrum of the R-R interval (ECG based Heart Rate Variability power spectrum) in predefined time window. | 4 |
| 22. | ECG Freq. | R-R Variability LF/HF | Ratio between LF (0.04 Hz-0.15 Hz) ECG-HRV power spectrum and HF (0.15 Hz-0.4 Hz) ECG-HRV power spectrum in predefined time window. | 1 |
| 23. | ECG Freq | ECG-RSA (Respiratory sinus arrhythmia) | The frequency of dominant peak at HF (0.15 Hz-0.4 Hz) band of ECG-HRV power spectrum in predefined time window. | 1 |
| 24. | ECG Freq. | RRI Variability wavelet analysis | Wavelet analysis of the R-R interval variability. | 1 |
| 25. | ECG Freq. | Alpha | Slope of HRV power spectrum in predefined time window | 1 |
| 26. | ECG Freq. | Beta | Slope of the log of HRV power spectrum in predefined time window | 1 |
| 27. | ECG-PPG | ECG-PPG PTT Pulse Transition time | The time interval between R peak of ECG signal and Peak of PPG signal (PTT or rPTT), mean interval and STD (variability) of intervals in predefined time window. | 3 |
| 28. | Temp | Temperature amplitude, mean amplitude and std of amplitude | The amplitude of the temperature signal, mean amplitude and STD of amplitude in predefined time window. | 2 |
| 29. | Temp | Temp Peak (P) amplitude, mean amplitude and std of amplitude | The amplitude of the Peak (P) of temperature signal, mean amplitude and STD of amplitude in predefined time window. | 1 |
| 30. | Temp | PP interval, mean and std (variability) of interval | The time interval between peak to peak of temperature signal, mean interval and STD (variability) of intervals in predefined time window. | 1 |
| 31. | Temperature | Spectrum of the temperature signal | Power Spectrum of the temperature signal in predefined time window. | 1 |
| 32. | Temperature | Peak Amplitude | The amplitude of the highest peak of the power spectrum in predefined time window. | 1 |
| 33. | Temperature | Peak Frequency | The frequency of the highest peak of the power spectrum in predefined time window. | 1 |

TABLE 1-continued list of optional plurality of features

| # | Signal | Feature | Description | Number of features |
|---|--------|---------|-------------|--------------------|
| 34. | Respiratory | Upper peak amplitude, mean amplitude and STD of amplitude | The upper peak amplitude, mean amplitude and STD of amplitude of the upper peaks in predefined time window. The upper peak represent the depth of respiration. | 3 |
| 35. | Respiratory | Lower Peak amplitude, mean amplitude and STD of amplitude | The lower peak amplitude, mean amplitude and STD of amplitude of the lower peaks in predefined time window. The lower peaks represent the depth of breath release. | 2 |
| 36. | Respiratory | Respiratory rate, mean rate and std rate | The rate, mean rate and STD of rate in predefined time window. The rate is 1/ Peak-to-peak interval. | 3 |
| 37. | BP | BP Peak (P) and Trough (T) amplitude, mean amplitude and std of amplitude | The amplitude of the Peak (P) and the Trough (T) of the NIBP signal, mean amplitudes and STD of amplitudes in predefined time window. Peak denotes a systolic blood pressure; Trough denotes a diastolic blood pressure. | 6 |
| 38. | EEG/EMG | Power of $\lambda, \beta, \gamma, \delta, \theta$ frequency bands | Power of the frequency bands of power spectrum of EEG/fEMG signal in predefined time segment. Frequency range of different bands [Hz]: delta, $\delta$ 0.5-4 theta, $\theta$ 4-8 alpha, $\alpha$ 8-14 beta, $\beta$ 14-30 gamma $\gamma$, 30-70 | 4 |
| 39. | EEG/EMG | Mean frequency | The sum of the product of the power spectrum values in predefined time segment and the frequencies, divided by the total power. | 1 |
| 40. | EEG/EMG | Peak frequency | The frequency of the highest peak of the power spectrum in predefined time segment. | 1 |
| 41. | EEG/EMG | Spectral Edge Frequency | The frequency below which x percent of the power are located. Typically x is in the range 75 to 95. | 1 |
| 42. | EEG/EMG | Approximate Entropy - | For details see (Bruhn, Ropcke and Hoeft 2000) | 1 |
| 43. | EEG/EMG | BSR—Burst Suppression ratio | The burst suppression ratio is the proportion of the suppression EEG in the analyzed epoch (usually one minute): $$BSR = \frac{\text{total time of suppression}}{\text{epoch length}} 100$$ | 1 |
| 44. | EEG/EMG | BcSEF | Burst compensated spectral edge frequency $$BcSEF = SEF\left(1 - \frac{BSR\%}{100\%}\right)$$ | 1 |
| 45. | EEG/EMG | WSMF | A generalized form of spectral edge frequency, referred to as weighted spectral median frequency (WSMF), edge frequency is calculated not necessarily from PSD but from amplitude spectrum, which is raised to the power p = [0.1 . . . 2.4]; second, the cutoff frequencies of the original spectrum are well-defined; and, third, factor r = [0:05 : : : 0:95] is used, the percentile of the spectrum (e.g., r = 0:5 for MF and r = 0:95 for SEF). | 1 |

TABLE 1-continued list of optional plurality of features

| # | Signal | Feature | Description | Number of features |
|---|--------|---------|-------------|---------------------|
| 46. | EEG/EMG | CUP | Canonical univariate parameter: frequency bins with a width of 3 Hz or classical frequency bands are optimally weighted to obtain the best possible correlation with the drugs' effect-site concentration as obtained from pharmacokinetic-pharmacodynamic (PK-PD) modeling $$CUP = \sum_{k=1}^{10} \gamma_k \log p_k$$ | 1 |
| 47. | EEG/EMG | SpEn - | Spectral Entropy $$SpEn = -\sum_{k}^{N} p_k \log p_k.$$ | 1 |
| 48. | EEG/EMG | BcSpEn - | Burst compensated Spectral Entropy $$BcSpEn = SpEn\left(1 - \frac{BSR(\%)}{100\%}\right).$$ | 1 |
| 49. | EEG/EMG | Beta Ratio | $$BetaRatio = \log \frac{\hat{P}_{30\text{-}47Hz}}{\hat{P}_{11\text{-}20Hz}}.$$ | 1 |
| 50. | EEG/EMG | Histogram parameters | Mean, Standard deviation, Kurtosis, Skewness of signal histogram in predefined time segment. | 4 |
| 51. | EEG/EMG | AR parameters | Parameters of AR representation (Schlogl 2006) | N |
| 52. | EEG/EMG | Normalized slope descriptors (Hjorth parameters) | NSD parameters can be defined by means of first and second derivatives. "Activity" is a measure of the mean power, "Mobility" is an estimate of the mean frequency and "Complexity" is an estimate of the bandwidth of the signal (frequency spread) (Hjorth 1973). | 3 |
| 53. | EEG/EMG | Barlow parameters | Parameters based on Barlow EEG model which is an alternative time frequency decomposition. Parameters such as Running Mean Frequency and Spectral Purity Index (Goncharova and Barlow 1990) | 3 |
| 54. | EEG/EMG | Wackermann parameters | Three multi-channel linear descriptors of EEG signal. spatial complexity ($\Omega$), field power ($\Sigma$) and frequency of field changes ($\Phi$) (Wackermann 1999) | 3 |
| 55. | EEG/EMG | Brain rate | Weighted Mean Frequency (Pop-Jordanova and Pop-jordanov 2005) | 1 |
| 56. | EEG/EMG | SynchFastSlow | $$SynchFastSlow = \log \frac{\hat{B}_{40\text{-}47Hz}}{\hat{B}_{0.5\text{-}47Hz}}.$$ The spectrum and bispectrum, derived from two-second epochs, are smoothed using a running average against those calculated in the previous minute. 3 minutes window is required to obtain a consistent estimate of the bicoherence. | 1 |
| 57. | EEG/EOG | 80 Hz frequency in EEG near the eyes | Ocular microtremor (OMT) is a constant, physiological, high frequency (peak 80 Hz), low amplitude (estimated circa 150-2500 nm) eye tremor. | 1 |

TABLE 1-continued list of optional plurality of features

| # | Signal | Feature | Description | Number of features |
|---|---|---|---|---|
| 58. | EMG | Spectrum analysis - | Power of the frequency bands of power spectrum of EMG signal in predefined time segment. Frequency range of different bands [Hz]: | 1 |
| 59. | EMG | mean frequency | The sum of the product of the power spectrum values in predefined time segment and the frequencies, divided by the total power. | 1 |
| 60. | EMG | Peak frequency | The frequency of the highest peak of the power spectrum in predefined time segment. | 1 |
| 61. | EMG | Total power | The sum of the power spectrum within the epoch | 1 |
| 62. | EMG | Spontaneous lower oesophageal contractions (SLOC) | Lower oesophageal contractility (LOC). Spontaneous lower oesophageal contractions (SLOC) are non-propulsive spontaneous contractions mediated via vagal motor nuclei and reticular activating system in the brain stem. The frequency of these movements is increased as the dose of the anaesthetic is reduced. (Thomas and Evans 1989) | 1 |
| 63. | Airway CO2 | Average/ Variability | End tidal Carbon Dioxid (anesthesia) | 2 |
| 64. | Airway Gases | Average | End tidal sevofluane (anesthesia) | 1 |
| 65. | accelerometer X, Y, Z θ | Average value, Variability | accelerometer X, Y, Z theta, movement analysis | 12 |

Within the context of the present invention the term normalization refers to a signal processing or preprocessing technique as is known and accepted in the art for manipulating a physiological signal and/or feature. Normalization process for example comprises but is not limited to feature normalization to removes a subject's baseline; feature normalization to normalize a subject's baseline feature variability, feature normalization to remove a subject's baseline feature mean, feature normalization which removes the feature mean and normalize the feature to variability; feature normalization which normalize the feature value into a value between [0,1]. Most preferably normalization is performed following feature extraction and is proceeded by at least one or more signal preprocessing stages for example including but not limited to raw data preprocessing, optionally by noise filtering and/or artifact reduction, then features or the like are extracted and finally normalized. Optionally and preferably, normalization may be utilized for either a historical data set or the current data set. Optionally normalization may be performed on any data, parameters, variables and or features associated with the method and system of the present invention for example including but not limited to kurtosis, skewness, higher order moments and cummulants, probability distribution functions associated with a feature or the like.

Within the context of the present invention the term feature selection and dimensionality reduction refers to the process and/or technique of identifying, abstracting, representing or manipulating a plurality of physiological features and/or physiological signals in a more compact and/or reduced form. Optionally, in the process of feature selection and dimensionality reduction the number of physiological features and/or signals used with the system and method of the present invention is reduced.

Optionally and preferably feature selection and dimensional reduction techniques optionally employed within the system and method of the present invention may be linear or nonlinear, for example including but are not limited to Multi Dimensional Scaling (Borg, et. al., 2005), Principal Component Analysis (PCA), Sparse PCA (SPCA), Fisher Linear Discriminant Analysis (FLDA), Sparse FLDA (SFLDA), Kernel PCA (KPCA) (Scholkopf, et al., 1998), ISOMAP (Tenenbaum, et al., 2000), Locally Linear Embedding (LLE) (Roweis, et al., 2000), Laplacian Eigenmaps (Belkin, et al., 2003), Diffusion Maps (Coifman, et al., 2005), Hessian Eigenmaps (Donoho, et al., 2003), Independent Component Analysis (ICA), Factor analysis (FA), Hierarchical Dimensionality Reduction (HDR), Sure Independence Screening (SIS), Fisher score ranks, t-test rank, Mann-Whitney U-test taken alone or in any combination thereof or the like feature selection and dimensionality reduction techniques as is known and accepted in the art.

Within the context of the present invention the term classification refers to the analysis performed according to the system and method of the present invention to identify and or determine the physiological state of a subject with respect to pain. Optionally, the classification may be rendered in at least two and optionally a plurality of classes associated with pain. Optionally and preferably a plurality of classification techniques also optionally referred to herewith as classifiers may be utilized according to the system and method of the present invention as is known and accepted in the art or in any combination thereof for example including but is not limited to Nearest Shrunken Centroids (NSC)

(Tibshirani, et al., 2002), Classification and Regression Trees (CART) (Hastie, et al., 2009), ID3, C4.5, Multivariate Additive regression splines (MARS), Multiple additive regression trees (MART), Nearest Centroid (NC) classifier (Hastie, et al., 2009), Shrunken Centroid Regularized Linear Discriminate and Analysis (SCRLDA) (Guo, et al., 2007), Random Forest (Breiman, 2001), Boosting (Hastie, et al., 2009), Bagging Classifier (Breiman, 1996), AdaBoost, RealAdaBoost, LPBoost, TotalBoost, BrownBoost, MadaBoost, LogitBoost, GentleBoost, RobustBoost, Support Vector Machine (SVM) (Vapnik, 1998), kernelized SVM, Linear classifier, Quadratic Discriminant Analysis (QDA) classifier, Naive Bayes Classifier and Generalized Likelihood Ratio Test (GLRT) classifier with plug-in parametric or non-parametric class conditional density estimation, k-nearest neighbor, Radial Base Function (RBF) classifier, Multilayer Perceptron classifier, Bayesian Network (BN) classifier (Hastie, et al., 2009) (Bishop, 2006) or the like as are known and accepted in the art.

Optionally and preferably classification is performed using a classifier adept at multi-class classification. Optionally, multi-class classification may be adapted from binary classifier as is known and accepted in the art. Optionally binary classifiers may be adapted to perform a multi-class classification by reducing the multi-class problem to a plurality of multiple binary problems using methods as is known and accepted in the art for example including but not limited to one-vs-one with voting schemes by majority vote or pairwise coupling, one-vs-rest, Error Correcting Output Codes, or the like as is described and known in the art (Bishop, 2006) (Hastie, et al., 2009).

Optionally hierarchical multi-class classification may be performed as a tree structure having a single parent class or directed acyclic graph structure having at least one or more parental class.

Most preferably, the classifier is trained on a "training set". Optionally the training set may comprise data for classification that is made available from a plurality of sources, for example including but not limited to publicly available databases, proprietary clinical trials data, on site recorded data from at least one or more subject. Most preferably, the training set comprises input and output signals that mimic the input and output signals of the pain classifier according to the present invention. Most preferably the input signals comprising the training set are similar in nature to the expected input, of a pain classifier according to the present invention. Optionally and preferably the training set input signals comprise data similar to the features associated with a extracted feature vector according to the present invention, and/or a priori data as described above. Most preferably the output signals comprising the training set are similar in nature to the expected output from a pain classifier, according to the present invention. Most preferably, the training set is compiled by a pain expert for example a physician or other skilled person in the art of pain detection. Optionally, the training set is complied during a clinical trial comprising controlled pain stimuli.

Within the context of the present invention the term learning and or training refers to the process of training a pain classifier based on a given training, as is known and accepted in the art. Most preferably, the training process will provide for classifying previously unseen input data, not from the training set, with sensitivity and specificity optionally similar and more preferably better than the performances of a human operator.

A preferred embodiment of the present invention provides for a system and method for detecting, classifying and monitoring pain. Most preferably, the system and method of the present invention utilizes a collection of features referred to as a great plurality of features, hereinafter referred to as GPF, optionally comprising at least 9 physiological features, for detecting, classifying and identifying pain level. Optionally and preferably, a priori data, as described above, may be coupled with the GPF to facilitate pain monitoring and detection.

Optionally a plurality of features (GPF) providing for pain classification according to embodiments of the present invention may comprise a plurality of features corresponding to and extracted from at least three or more physiological signals, as depicted in Table 1.

Preferably a first vector comprising a plurality of features (GPF) includes features, and/or feature groups originating from at least three physiological signals including PPG, GSR and at least one or more physiological signals chosen from the group consisting: of skin temperature, ECG, Respiration, EMG, and EEG/FEMG. Optionally and most preferably a first vector of features may be built from the features associated with at least 1 (one) of 32 (thirty two) optional physiological signal groups, for example including but not limited to: PPG-GSR; PPG-GSR-TEMP; PPG-GSR-ECG; PPG-GSR-RESP; PPG-GSR-EMG; PPG-GSR-EEG/FEMG; PPG-GSR-TEMP-ECG; PPG-GSR-TEMP-RESP; PPG-GSR-TEMP-EMG; PPG-GSR-TEMP-EEG/FEMG; PPG-GSR-ECG-RESP; PPG-GSR-ECG-EMG; PPG-GSR-ECG-EEG/FEMG; PPG-GSR-RESP-EMG; PPG-GSR-RESP-EEG/FEMG; PPG-GSR-EMG-EEG/FEMG; PPG-GSR-TEMP-ECG-RESP; PPG-GSR-TEMP-ECG-EMG; PPG-GSR-TEMP-ECG-EEG/FEMG; PPG-GSR-TEMP-RESP-EMG; PPG-GSR-TEMP-RESP-EEG/FEMG; PPG-GSR-ECG-RESP-EMG; PPG-GSR-ECG-RESP-EEG/FEMG; PPG-GSR-ECG-EMG-EEG/FEMG; PPG-GSR-RESP-EMG-EEG/FEMG; PPG-GSR-TEMP-EMG-EEG/FEMG; PPG-GSR-TEMP-ECG-RESP-EMG; PPG-GSR-TEMP-ECG-RESP-EEG/FEMG; PPG-GSR-TEMP-ECG-EMG-EEG/FEMG; PPG-GSR-TEMP-RESP-EMG-EEG/FEMG; PPG-GSR-ECG-RESP-EMG-EEG/FEMG; PPG-GSR-TEMP-ECG-RESP-EMG-EEG/FEMG; or the like group or combination of physiological signals.

Optionally and preferably each of the physiological signals namely, PPG, GSR, skin temperature, ECG, Respiration, EMG, and EEG/FEMG, or the like may individually provide a feature and/or a group of features based on the physiological signal itself, each feature group defined as follows according to its physiological signal, as follows:

PPG features, for example include but not limited to:
PPG Peak (P) amplitude, Trough (T) amplitude, mean PPG Peak (P) amplitude, and std of PPG Peak (P) amplitude, mean Trough (T) amplitude, and std of Trough (T) amplitude, PPG peak to peak time intervals, PPG peak to peak interval mean and PPG peak to peak interval std; power spectrum of the PPG peak to peak intervals: VLF Power, LF Power and HF Power;

GSR features, table 1, for example including but not limited to:
GSR amplitude, GSR mean amplitude and GSR amplitude std; GSR Peak (P) amplitude, mean Peak (P) amplitude and Peak (P) amplitude std; GSR peak to peak time intervals, mean GSR peak to peak time interval; and GSR peak to peak time intervals std; Phasic EDA: amplitude, mean amplitude and std of amplitude;

Skin temperature features, Table 1, for example including but not limited to:
Temperature amplitude, mean amplitude and std of amplitude; Temp Peak (P) amplitude, mean amplitude and std of amplitude; Temperature peak to peak time intervals, mean and std (variability) of interval;

ECG features, Table 1, for example including but not limited to:
ECG-PPG PTT Pulse Transition time; ECG R to R time intervals, mean and std (variability) of intervals; Power of VLF, LF and HF frequency bands of power spectrum of the ECG R to R intervals (heart rate variability);
Respiration features, Table 1, for example including but not limited to: Upper peak amplitude, mean amplitude and STD of amplitude, Respiratory rate, mean rate and std rate
EMG features for example including but not limited to:
Power of the frequency bands of power spectrum of EMG signal; EMG Power Spectrum Mean frequency;
EMG Power Spectrum Highest Peak Frequency;

EEG/FEMG features, table 1, for example including but not limited to:
Power of the alpha (α), beta (β), gamma (γ), delta (δ), theta (θ) frequency bands of power spectrum of EEG/FEMG signal; EMG Power Spectrum Mean frequency;
EMG Power Spectral edge frequency 'Coherence between 2 or more EEG/FEMG channels;

Preferably any combination of the feature groups, defined above, and most preferably a combination of features according to at least one or more of the above referenced 32 (thirty two) physiological signal groups may be utilized to form a first vector of feature upon which classification will be based and performed according to embodiments of the present invention.

Optionally the system and method of the present invention provide for classification of pain into a plurality of classes, most preferably comprising at least 2 classes. Optionally, pain may be categorized into 3 or more classification groups. Optionally, each pain classification may be further provided with scalable scoring method optionally using a numerical scoring for example including a scale of 1 to 10, a scale of 1-100 or the like. Optionally, pain classification scoring may be further correlated to a subjective pain scaling and/or scoring schemes for example including but not limited to Visual Analog Scale (VAS), Numeric Pain Scale (NPS), verbal scale or the like as is known in the art. Optionally, pain may be categorized according to a disease, stimulus and or medicament for example pain associated with cancer would be classified in one class while pain associated with diabetes would be classified in another class.

Optionally, the system and method according to the present invention may be adapted to and/or provide for pain monitoring, classification and/or detection according to at least one or more optional sources of pain for example including but not limited to stimulus, medicament or a disease.

An optional embodiment of the system and method according to the present invention is provided with a GPF that are most preferably abstracted from a plurality of physiological signals for example including but not limited to blood pressure, respiration, internal or skin temperature, pupil diameter, GSR, and signals received from ECG, PPG, EOG, EGG, EEG, EMG, EGG, LDV, capnograph and accelerometer or the like physiological signal as is known and accepted in the art.

Optionally and preferably, GPF is abstracted from a plurality of physiological signals using at least one or more feature extraction techniques as described above and as is known and accepted in the art.

Optionally, the GPF according to the present invention may be further processed using at least one or more feature selection and dimensionality reducing techniques as described above and as is known and accepted in the art, most preferably providing a set of parameters based on the GPF that are preferably then utilized for classification.

Most preferably, classification is provided by classifiers as described above and as is known and accepted in the art optionally, the classifier may provide for linear and/or non-linear classification. Optionally the classifier provides for classification of at least 2 classes. Optionally and preferably the classifier provides for multi-class classification of a plurality of classes An optional embodiment for a system for pain monitoring and detection according to the present invention comprises a signal acquisition module, a processing module and a communication module. Optionally the system may further comprise a display module. Most preferably, signal acquisition comprises a plurality of optional sensors and/or transducers for measuring and or obtaining physiological signals and data. Most preferably, processing module provides for processing the physiological signals provided through the acquisition module, for example to abstract from the signals the GPF. Optionally, the processing module provide for all processing of signals for example including but not limited to feature abstraction, preprocessing, feature selection and dimensionality reduction and classification. Optionally and preferably, the communication module is provided to communicate the classification results from the processing module. Optionally the communication module may provide for communicating results to an auxiliary person, system, device, machine, processor for example including but not limited to a higher processing center, person, caregiver, call center, or the like in any combination thereof.

Optionally, the display module is provided to display and/or communicate the classification results from the processing module. Optionally, display module comprise a display for example including but not limited to a visual display, printed display or audible display, or the like for displaying and conveying pain monitoring. Optionally, processing module may be realized as a wired or wireless device for example including but not limited to a computer, a server, PDA, mobile telephone, display, printout or the like as is known and accepted in the art.

An optional embodiment according to the present invention provides for a method for detecting and classifying the pain status of a patient by analyzing a plurality of physiological signals, the method comprises:

a. Signal acquisition for acquiring the plurality of physiological signals; and b. pre-processing the acquired plurality of physiological signals to improve signal quality comprising at least one or more chosen from the group consisting of synchronization, noise filtering, artifact reduction, therein forming a plurality of pre-processed physiological signals; and c. processing the pre-processed plurality of physiological signals, the processing comprising:
  i. feature extraction from at least three or more physiological signals including PPG, GSR and at least one or more physiological signals chosen from the group consisting: of skin temperature, ECG, Respiration, EMG, and EEG/FEMG to facilitate detection of pain in a patient; and forming a first vector comprising a set of extracted features; and
  ii. transforming the first vector to a second vector wherein pain detection is performed based on the second vector and wherein the transformation comprises normalization, feature selection and dimensionality reduction techniques; and iii. detecting the pain status of a patient by applying a classification function to classify the second vector into at least two classes of pain.

Optionally the method further comprises communicating the detected pain status of the patient to at least one or more for example including but not limited to a higher processing center, person, caregiver, call center and any combination thereof.

Optionally and preferably the first vector comprises a plurality of features including parameters extracted from the PPG and GSR physiological signals including:
a. PPG features chosen from the group consisting of:
  i. PPG Peak (P) amplitude, Trough (T) amplitude, mean PPG Peak (P) amplitude, and std of PPG Peak (P) amplitude, mean Trough (T) amplitude, and std of Trough (T) amplitude; and
  ii. PPG peak to peak time intervals, PPG peak to peak interval mean and PPG peak to peak interval std; and
  iii. power spectrum of the PPG peak to peak intervals: VLF Power, LF Power and HF Power; and
b. GSR features chosen from the group consisting of:
  i. GSR amplitude, GSR mean amplitude and GSR amplitude std; and
  ii. GSR Peak (P) amplitude, mean Peak (P) amplitude and Peak (P) amplitude std; and
  iii. GSR peak to peak time intervals, mean GSR peak to peak time interval; and GSR peak to peak time intervals std; and
  iv. Phasic EDA: amplitude, mean amplitude and std of amplitude.

Optionally, the first vector further comprises a group of features extracted from one of the physiological signals selected from the group consisting of skin temperature, ECG, Respiration, EMG, and EEG/FEMG.

Optionally, the first vector further comprises a group of features extracted from two of the physiological signals selected from the group consisting of skin temperature, ECG, Respiration, EMG, and EEG/FEMG.

Optionally, the first vector further comprises a group of features extracted from three of the physiological signals selected from the group consisting of skin temperature, ECG, Respiration, EMG, and EEG/FEMG.

Optionally, the first vector further comprises a group of features extracted from four of the physiological signals selected from the group consisting of skin temperature, ECG, Respiration, EMG, and EEG/FEMG.

Optionally, the first vector further comprises a group of features extracted from the physiological signals essentially consisting of PPG, GSR, skin temperature, ECG, Respiration, EMG, and EEG/FEMG.

Optionally and preferably, extracted features are chosen form at least one or more of the feature groups corresponding to a physiological signal chosen from the group consisting of skin temperature, ECG, Respiration, EMG, and EEG/FEMG, the feature groups comprising:
a. Skin temperature features chosen from the group of consisting:
  i. Temperature amplitude, mean amplitude and std of amplitude; and
  ii. Temp Peak (P) amplitude, mean amplitude and std of amplitude; and
  iii. Temperature peak to peak time intervals, mean and std (variability) of interval; and
b. ECG features chosen from the group of consisting:
  i. ECG-PPG PTT Pulse Transition time; and
  ii. ECG R to R time intervals, mean and std (variability) of intervals; and
  iii. Power of VLF, LF and HF frequency bands of power spectrum of the ECG R to R intervals (heart rate variability); and
c. Respiration features chosen from the group of consisting of:
  i. Upper peak amplitude, mean amplitude and STD of amplitude; and
  ii. Respiratory rate, mean rate and std rate; and
d. EMG features chosen from the group of consisting of:
  i. Power of the frequency bands of power spectrum of EMG signal; and
  ii. EMG Power Spectrum Mean frequency; and
  iii. EMG Power Spectrum Highest Peak Frequency; and
e. EEG/FEMG features chosen from the group of consisting of:
  i. Power of the alpha ($\alpha$), beta ($\beta$), gamma ($\gamma$), delta ($\delta$), theta ($\theta$) frequency bands of power spectrum of EEG/FEMG signal; and
  ii. EMG Power Spectrum Mean frequency; and
  iii. EMG Power Spectral edge frequency; and
  iv. Coherence between 2 or more EEG/FEMG channels.

Optionally, signal acquisition facilitates acquiring physiological signals with a plurality of sensors for example including but not limited to: ECG, PPG, blood pressure, respiration, internal body temperature, skin temperature, EOG, pupil diameter monitoring, GSR, EEG/FEMG, EMG, EGG, LDV, capnograph and accelerometer, or the like. Optionally and preferably, the physiological signals are pre-processed and processed, facilitating said detection and classification of pain status.

Optionally the method further comprises, obtaining and processing a priori data for facilitating the detection and classification of pain status. Optionally a priori data may for example include but is not limited to patient associated data, historical data, data from the group consisting of data supplied by the physician's, environmental parameters, patient parameters, disease, stimulus and medicament, any combination thereof, or the like.

Optionally, the second vector further comprises a priori data.

Optionally, pain classification may be classified into groups for example including but not limited to: at least two classes, at least three classes, pain/no-pain states, graduated scale, scale of 1 to 10, a scale of 1-100, subjective pain scaling schemes, subjective scoring schemes, Visual Analog Scale (VAS), Numeric Pain Scale (NPS) and verbal scale, or the like.

Optionally, dimensionality reducing transformation comprises a linear or non-linear transformation, for example including but is not limited to: Multi Dimensional Scaling (MDS), Principal Component Analysis (PCA), Sparse PCA (SPCA), Fisher Linear Discriminant Analysis (FLDA), Sparse FLDA (SFLDA), Kernel PCA (KPCA), ISOMAP, Locally Linear Embedding (LLE), Laplacian Eigenmaps, Diffusion Maps, Hessian Eigenmaps, Independent Component Analysis (ICA), Factor analysis (FA), Hierarchical Feature selection and dimensionality reduction (HDR), Sure Independence Screening (SIS), Fisher score ranks, t-test rank, Mann-Whitney U-test or any combination thereof.

Optionally classification function may be a linear or non-linear transformation for example including but not limited to: Nearest Shrunken Centroids (NSC), Classification and Regression Trees(CART), ID3, C4.5, Multivariate Additive regression splines (MARS), Multiple additive regression trees (MART), Nearest Centroid (NC), Shrunken Centroid Regularized Linear Discriminate and Analysis (SCRLDA), Random Forest, Boosting, Bagging Classifier, AdaBoost, RealAdaBoost, LPBoost, TotalBoost, BrownBoost, MadaBoost, LogitBoost, GentleBoost, RobustBoost, Support Vector Machine (SVM), kernelized SVM, Linear classifier, Quadratic Discriminant Analysis (QDA) classifier, Naïve Bayes Classifier and Generalized Likelihood Ratio Test (GLRT) classifier with plug-in parametric or non-parametric class conditional density estimation, k-nearest neighbor, Radial Base Function (RBF) classifier, Multilayer Perceptron classifier, Bayesian Network (BN) classifier, multi-class classifier adapted from binary classifier with one-vs-one majority voting, one-vs-rest, Error Correcting Output Codes, hierarchical multi-class classification, Committee of classifiers, or the like, and any combination thereof.

Optionally, the method according to an optional embodiment of the present invention comprises: feature selection and dimensionality reduction provided by Hierarchical Dimensionality Reduction (HDR); and classification provided by a Random Forest classifier.

Optionally, the method according to an optional embodiment of the present invention comprises, feature selection and dimensionality reduction provided by Fisher Score rank, and SFLDA and classification provided by a RealAdaboost classifier within a Boosting framework.

Optionally classification may be adapted for pain experienced with a particular disease, stimulus or medicament.

Optionally, the status of pain may be adapted for a patient in various states of consciences chosen from the group consisting of: sedated, partially sedate and awake, semi-awake.

An optional embodiment according to the present invention provides for a system for detecting and classifying the pain status of a patient by analyzing a plurality of physiological signals comprising:
 a. a signal acquisition module comprising a plurality of sensors and/or transducers for measuring and/or obtaining the at least three or more physiological signals and a priori data from a subject; and
 b. a processing module for processing the physiological signals, comprising:
  i. pre-processing the acquired plurality of physiological signals to improve signal quality comprising at least one or more tools for example including but not limited to synchronization, noise filtering, artifact reduction therein forming a pre-processed plurality of physiological signals; and
  ii. processing the pre-processed plurality of physiological signals comprising:
  iii. feature extraction from at least three or more physiological signals including PPG, GSR and at least one or more physiological signals chosen from the group consisting: of skin temperature, ECG, Respiration, EMG, and EEG/FEMG to facilitate detection of pain in a patient; and forming a first vector comprising a set of extracted features; and
  iv. transforming the first vector to a second vector wherein pain detection is performed based on the second vector and wherein the transformation comprises normalization and feature selection and dimensionality reduction techniques; and
  v. detecting the pain status of a patient by applying a classification function to classifying the second vector into at least two classes of pain; and
 c. a communicating module for communicating the detected pain status of the patient to at least one or more for example including but not limited to a higher processing center, person, caregiver, call center and any combination thereof.

Optionally, the system may further comprise a display module for displaying the detected and classified pain stimulus.

Optionally and preferably, the processing module provides for extracting features form at least one or more of the feature groups corresponding to a physiological signal chosen from the group consisting of skin temperature, ECG, Respiration, EMG, and EEG/FEMG, the feature groups comprising:
 a. Skin temperature features chosen from the group of consisting:
  i. Temperature amplitude, mean amplitude and std of amplitude; and
  ii. Temp Peak (P) amplitude, mean amplitude and std of amplitude; and
  iii. Temperature peak to peak time intervals, mean and std (variability) of interval; and
 b. ECG features chosen from the group of consisting:
  i. ECG-PPG PTT Pulse Transition time; and
  ii. ECG R to R time intervals, mean and std (variability) of intervals; and
  iii. Power of VLF, LF and HF frequency bands of power spectrum of the ECG R to R intervals (heart rate variability); and
 c. Respiration features chosen from the group of consisting of:
  i. Upper peak amplitude, mean amplitude and STD of amplitude; and
  ii. Respiratory rate, mean rate and std rate; and
 d. EMG features chosen from the group of consisting of:
  i. Power of the frequency bands of power spectrum of EMG signal; and
  ii. EMG Power Spectrum Mean frequency; and
  iii. EMG Power Spectrum Highest Peak Frequency; and
 e. EEG/FEMG features chosen from the group of consisting of:
  i. Power of the alpha ($\alpha$), beta ($\beta$), gamma ($\gamma$), delta ($\delta$), theta ($\theta$) frequency bands of power spectrum of EEG/FEMG signal; and
  ii. EMG Power Spectrum Mean frequency; and
  iii. EMG Power Spectral edge frequency; and
  iv. Coherence between 2 or more EEG/FEMG channels.

Optionally the system according to the present invention further comprises a signal acquisition module that facilitates acquiring physiological signals with a plurality of sensors for example including but not limited to: ECG, PPG, blood pressure, respiration, internal body temperature, skin temperature, EOG, pupil diameter monitoring, GSR, EEG/FEMG, EMG, EGG, LDV, capnograph and accelerometer, or the like. Optionally, the physiological signals may be pre-processed and processed facilitating the detection and classification of pain status.

Unless otherwise defined the various embodiment of the present invention may be provided to an end user in a plurality of formats, platforms, and may be outputted to at least one of a computer readable memory, a computer display device, a printout, a computer on a network or a user.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and/or the ability to execute one or more instructions may be described as a computer, including but not limited to a PC (personal computer), a server, a minicomputer, a cellular telephone, a smart phone, a PDA (personal data assistant), a pager. Any two or more of such devices in communication with each other, and/or any computer in communication with any other computer, may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3A-E are schematic block diagrams of optional embodiments of a system according to the present invention.

DESCRIPTION OF THE PREFERRED EMBODIMENTS

The present invention is of a system and a method for pain detection and monitoring most preferably detection and monitoring of pain is facilitated by processing physiological signals and features most preferably represented by a data vector comprising a great plurality of features. The principles and operation of the present invention may be better understood with reference to the drawings and the accompanying description.

For the sake of clearly throughout the figures similar labels and numbering scheme is used throughout for equivalent or similarly functioning elements.

Figure 1:
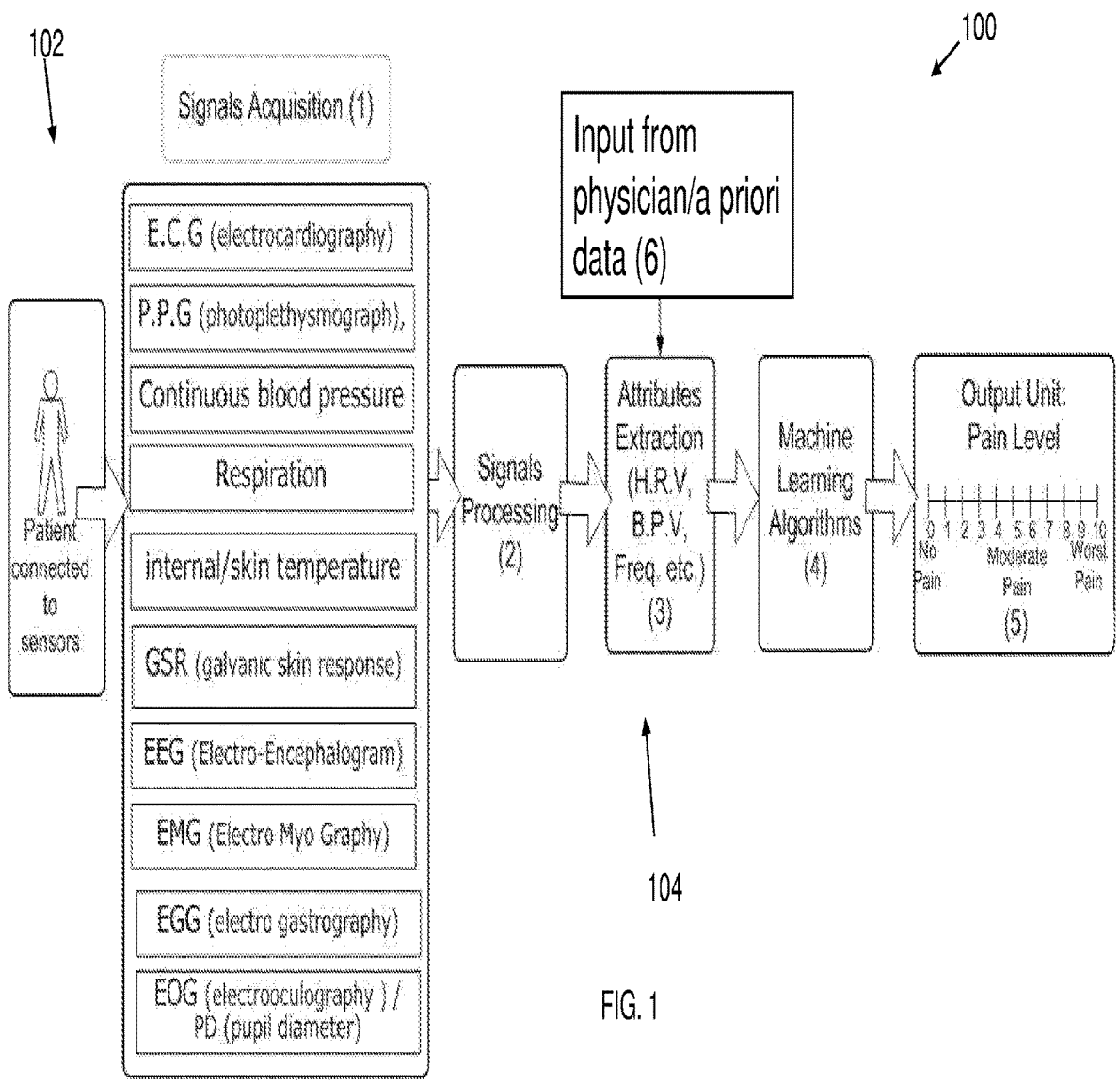
FIG. 1 is schematic block diagram of an exemplary system according to the present invention.

FIG. 1 is a schematic block diagram of an exemplary system 100 according to the present invention for pain monitoring comprising physiological signal acquisition module 102 and processing module 104.

Most preferably signal acquisition module 102 is provided for acquiring and measuring physiological measurements from a subject able to experience pain optionally including but not limited to a person is optionally provided with at least one or more preferably a plurality of sensor or transducers as are known and accepted in the art. Processing module 104 is most preferably provided with a plurality of sub-modules for example including but not limited to signal processing module 2, feature extraction module 3, machine learning module 4. Optionally and preferably signal processing module 2 provides for preprocessing of the acquired signal for example including but not limited to normalization, filtering, noise reduction, SNR optimization, domain transformations, statistical analysis, spectral analysis, wavelet analysis, or the like.

Optionally and preferably feature extraction module 3 is provided for extracting features associated with the signals acquired with module 102. Optionally and preferably, feature extraction module may be further provided with an a priori data sub-module 6 most preferably for providing data beyond the acquired signals for example including but not limited to physician and/or caregiver data, medical history, genetic predispositions data, medical records or the like a priori data. Most preferably feature extraction is provided by performing signal processing techniques as is known and accepted in the art to extract from a physiological signal relevant and pertinent data. For example, a ECG measured acquired in module 102 is processed to provide a plurality of features. For example including but not limited to HRV, complex analysis, cardiac output data or the like. Most preferably feature extraction module 3 from the GPF vector for further analysis, for example including the features depicted in Table 1 above Machine learning module 4 is provided to classify the feature vector set provided from module 3. Optionally, machine learning module 4 may provide for feature selection and dimensionality reduction wherein the GPF vector undergoes feature selection and dimensionality reduction to provide a second vector therein providing a representation of the GPF in a smaller dimension. Optionally and preferably feature selection and dimensionality reduction techniques for example include but are not limited to Multi Dimensional Scaling (MDS), Principal Component Analysis (PCA), Sparse PCA (SPCA), Fisher Linear Discriminant Analysis (FLDA), Sparse FLDA (SFLDA), Kernel PCA (KPCA), ISOMAP, Locally Linear Embedding (LLE), Laplacian Eigenmaps, Diffusion Maps, Hessian Eigenmaps, Independent Component Analysis (ICA), Factor analysis (FA), Hierarchical Dimensionality Reduction (HDR), Sure Independence Screening (SIS), Fisher score ranks, t-test rank, Mann-Whitney U-test taken alone or in any combination thereof, or as known and accepted in the art.

Optionally classification is performed on at least one of the GPF vector or a second vector comprising a dimensionally reduced version of GPF vector. Most preferably machine learning module 4 provides for pain classification into at least two or more classes, for example including pain and non-pain groups. Optionally, and preferably a plurality of optional classifiers may be used for example including but not limited Nearest Shrunken Centroids (NSC), Classification and Regression Trees (CART), ID3, C4.5, Multivariate Additive regression splines (MARS), Multiple additive regression trees (MART), Nearest Centroid (NC), Shrunken Centroid Regularized Linear Discriminate and Analysis (SCRLDA), Random Forest, Boosting, Bagging Classifier, AdaBoost, RealAdaBoost, LPBoost, TotalBoost, BrownBoost, MadaBoost, LogitBoost, GentleBoost, RobustBoost, Support Vector Machine (SVM), kernelized SVM, Linear classifier, Quadratic Discriminant Analysis (QDA) classifier, Naïve Bayes Classifier and Generalized Likelihood Ratio Test (GLRT) classifier with plug-in parametric or non-parametric class conditional density estimation, k-nearest neighbor, Radial Base Function (RBF) classifier, Multilayer Perceptron classifier, Bayesian Network (BN) classifier, multi-class classifier adapted from binary classifier with one-vs-one majority voting, one-vs-rest, Error Correcting Output Codes, hierarchical multi-class classification, Committee of classifiers or the like as are known and accepted in the art or any combination thereof.

Optionally classification may be further provided with a graded scoring relating the level of pain classified.

Output module 5 is provided to display or otherwise communicate the classification results provided by machine learning module 4. Optionally classification results may be displayed in a plurality of formats for example including printout, visual display cues, acoustic cues or the like. Optionally results may be displayed in graded or class formats, or the like.

Optionally output module may communicate the classification results to and external device for further processing, medical intervention or the like, for example classification results may be communicated to a drug administration device to automatically, semi-automatically, or manually control the drug delivery of a pain medicament, or to indicate to a caregiver to control, change, decrease or increase the dosage or delivery of a pain reducing drug.

Figure 2A:
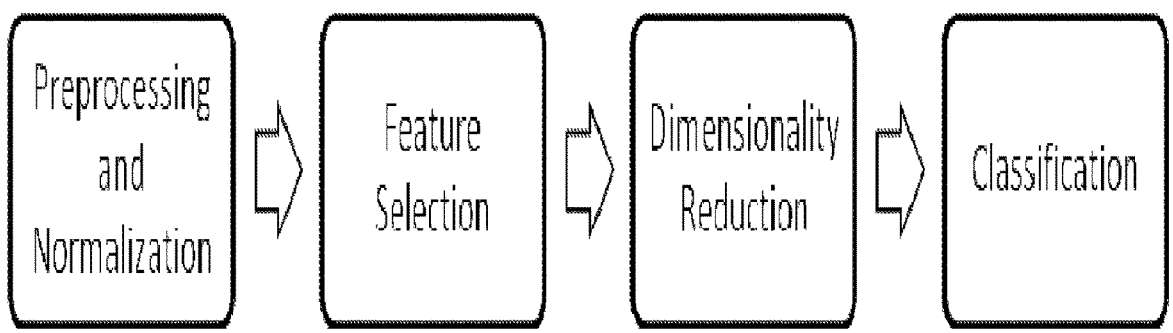
FIGS. 2A-C are schematic block diagram of the machine learning module of FIG. 1 in greater detail.
Figure 2B:
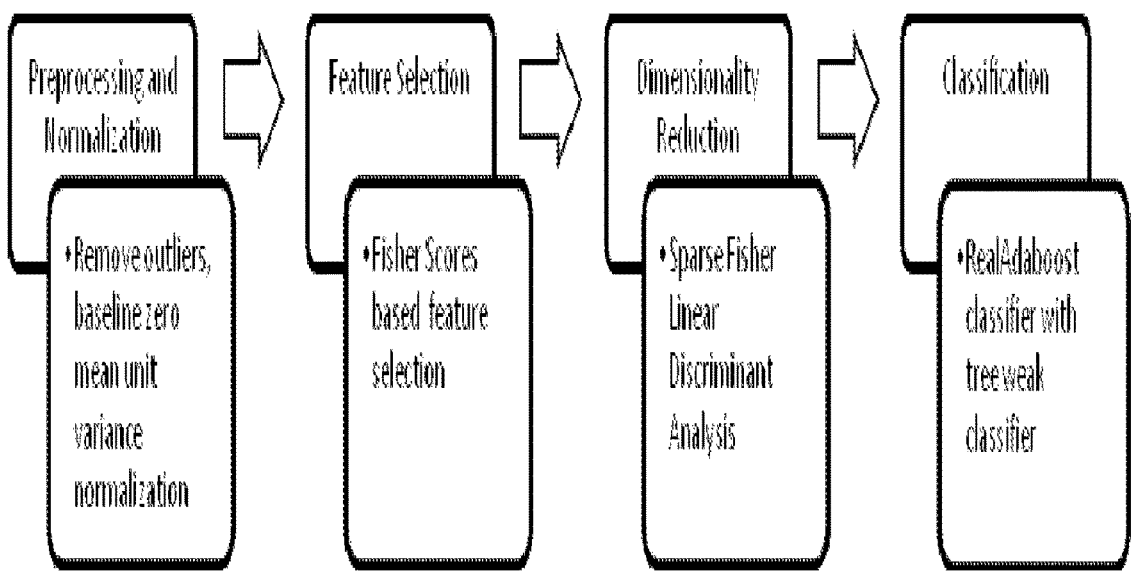
Figure 2C:
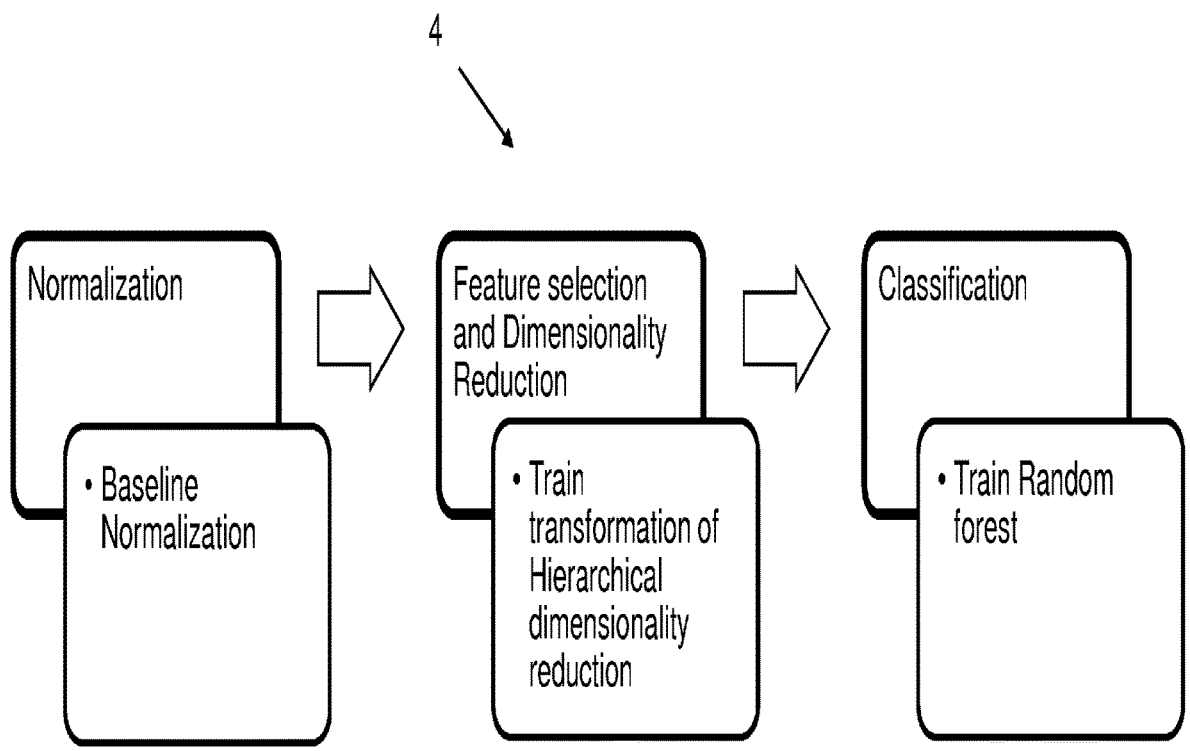

FIGS. 2A-C provide a further optional depiction of machine learning module 4 of the processing module 104 of FIG. 1 wherein the feature vector set provided from module 3 is processed, most preferably sequentially, with a plurality of machine learning sub-modules, for example, preprocessing and normalization sub-module, feature selection and dimensionality reduction sub-module and classification sub-module. Machine-learning sub-modules implements machine learning techniques and methods as is known and accepted in the art. Optionally, sub-modules of the machine learning module comprising preprocessing and normalization, feature selection and dimensionality reduction may be reorganized and provided in all possible combination.

FIG. 2B provides a depiction of a non limiting example of an optional embodiment of FIG. 2A, also described in Example 1 below, wherein the machine learning module 4 of the processing module 104 of FIG. 1 is provided by a collection of machine learning sub-modules. For example, preprocessing is provided by a plurality of actions including outlier removal and signal normalization utilizing baseline zero mean unit variance; feature selection is provided through the use of a Fisher score; dimensionality reduction is provided by Sparse Fisher Linear Discriminant Analysis (SFLDA) while classification is provided by a RealAdaboost classifier. Most preferably machine learning module 4 of FIG. 1 comprises at least one preprocessing sub-module, at least one feature selection and dimensionality reduction sub-module, and at least one classification sub-module; of the optional techniques described above, in any combination thereof as is know and accepted in the art.

FIG. 2C provides a depiction of a non limiting example of an optional embodiment of FIG. 2A, also described in Example 3 below, wherein the machine learning module 4 of the processing module 104 of FIG. 1 is provided by a collection of machine learning sub-modules. For example, preprocessing is provided by a plurality of actions including outlier removal and signal normalization utilizing baseline zero mean unit variance; feature selection and dimensionality reduction is provided by Hierarchical dimensionality reduction while classification is provided by a Random Forest classifier.

Figure 3A:
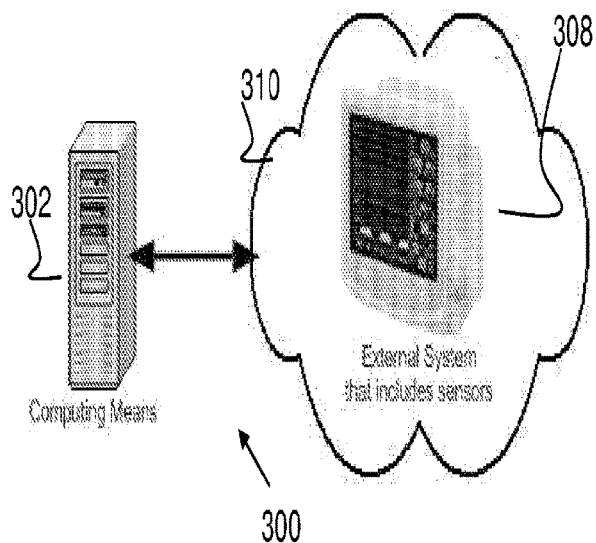
Figure 3E:
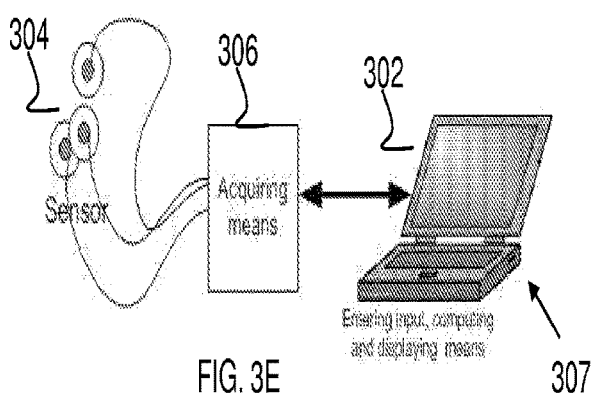
Figure 3D:
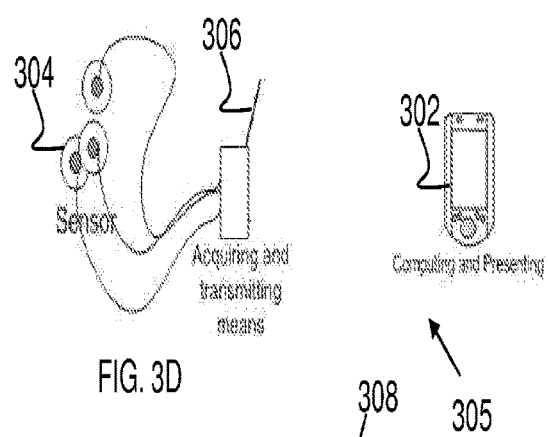
Figure 3B:
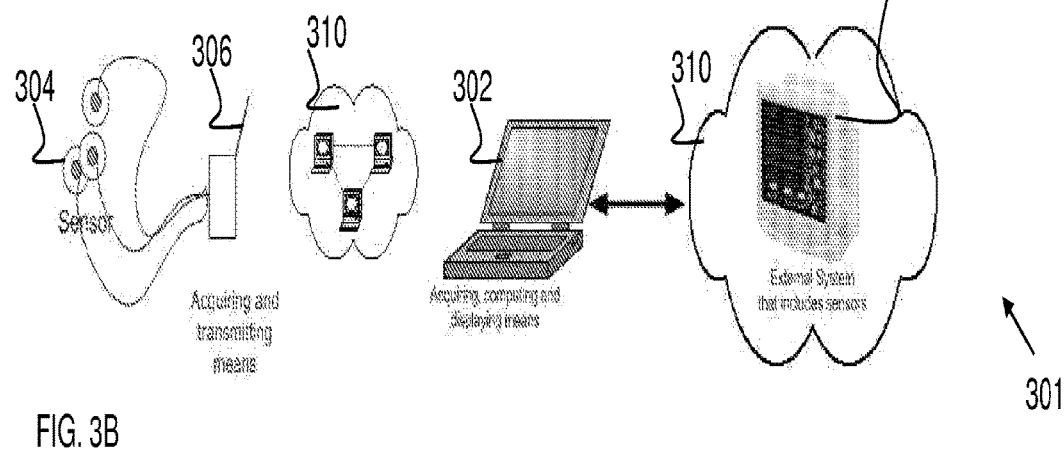

FIGS. 3A-E depicts optional hardware configurations of optional systems according to optional embodiments of the present invention as described in FIG. 1 above. FIGS. 3A-3E depicts different remote and local configurations of signal acquisition, processing and display. FIGS. 3A and 3E depicts systems that may be adapted to provide for a fully local system, FIGS. 3B and 3C depicts systems that may be optionally configured to be semi remote, while FIG. 3D depicts a system that may be adapted to be fully remote.

FIG. 3A depicts optional configuration system 300 comprising computer 302 and an external signal acquisition and display monitor 308, optionally and preferably communicating using communication protocol 310. Most preferably, monitor 308 comprises a stand alone or external monitor comprising signal acquisition and display that optionally and preferably provides for signal acquisition that is preferably processed with computer 302. Optionally and preferably computer 302 provides for the processing for pain monitoring and detection according to the present. invention. Optionally computer 302 may be realized as a processor, server or the like computing device as is known and accepted in the art. Optionally communication protocol 310 mediates communication and data exchange between computer 302 and external monitor 308 providing for pain classification. Optionally, communication protocol may be provided in a plurality of optional communication protocols as is known and accepted in the art for example including but not limited to wireless, wired, cellular, internet, Bluetooth, optical, IR or the like communication protocols as is known and accepted in the art. Optionally and preferably computer 302 provides for pain classification and monitoring according to the present invention while physiological signal acquisition and display is provided by monitor 308 most preferably monitor 308 acquires the signals, transmit them to processor 302 and optionally and preferably displays the classification result FIG. 3C depicts an optional system 303 similar in configuration to system 300 of FIG. 3A above wherein the physiological signals are preferably provided by both monitor 308 and acquisition transducers 304 wherein both are communicated to computer 302 for processing according to an optional method according to the present invention.

FIG. 3B depicts optional configuration system 301 comprising computer 302, signal acquisition transducers 304, physiological signal acquisition device 306, acquiring and displaying monitor 308 and communication protocol 310. Optionally signal acquisition transducer 304 is most preferably provided in the form of optional sensors dependent on the signal being acquired that is preferably coupled to signal acquisition device 306 most preferably to sample, amplify and process and record a physiological signal. Optionally and preferably device 306 is a mobile, optionally provided in a plurality of formats for example including but not limited to mobile telephone, PDA, hand held device, MP3 player, dedicated or converted device adept for receiving and communicating a physiological signal. Optionally device 306 comprises a processor for performing initial signal processing of the physiological signal. Optionally, device 306 does not comprise a processor adept for processing the sampled physiological signals and is linked using communication protocol 310 to higher processing centers, for example computer 302. Optionally, device 306 and computer 302 comprise a master slave processing protocols for processing the physiological signals sampled with system acquisition transducers 304. Optionally communication protocol 310 may be further facilitated through an interne connection. Optionally, computer 302 and display 308 may remote to the signal acquisition transducer 304 and device 306 relaying on communication protocol 310 to communicate therebetween. Optionally, computer 302 and acquiring and/or displaying monitor 308 may be implemented as a call center, telemedicine center, emergency medical center, or remote center for remote pain classification and detection for pain management.

FIG. 3D depicts system 305 for remote pain classification comprising a remote signal acquisition device 306 is utilized to acquire and communicate physiological signals for pain classification provided for with computer 302 provided in the form of a PDA comprising an intrinsic display. System 305 therefore provides a remote system comprising remote signal acquisition as well as remote signal processing and display. Conversely, FIG. 3E depicts system 307 comprising both local signal acquisition and processing.

Figure 4:
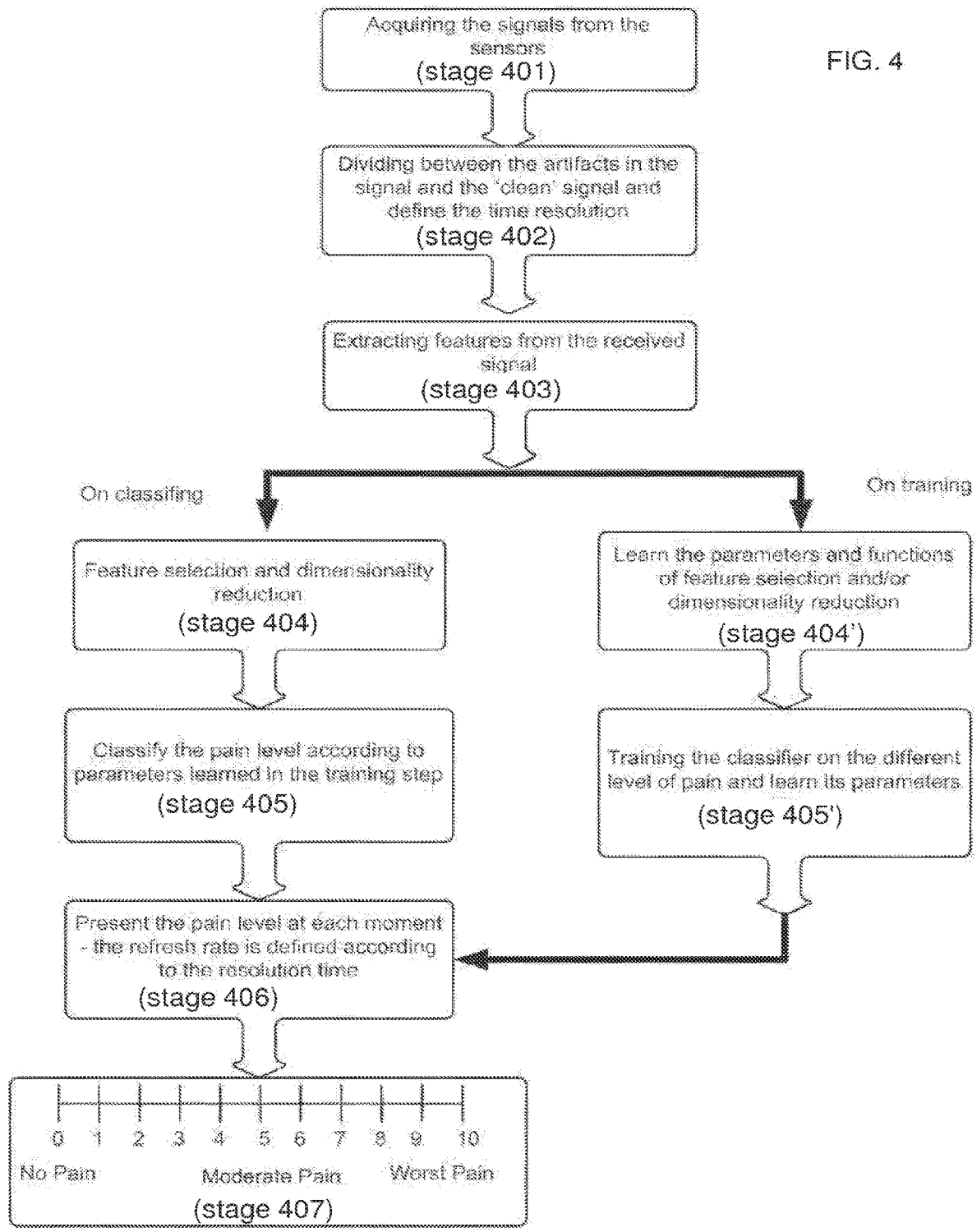
FIG. 4 is an exemplary method according to the present invention.

FIG. 4 shows a flowchart of an exemplary method according to the present invention for pain monitoring and classification. In stage 1 physiological signals are acquired, preferably a plurality of signals are obtained as previously described in FIG. 1 using a plurality of optional sensors and/or transducers. Next in stage 2, signal preprocessing is performed for example including but not limited to SNR optimization, signal normalization, filtering or the like. Next in stage 3, features extraction is performed to abstract and to preferably derive a great plurality of features GPF from the acquired physiological signals. Next classification processed is initiated with a training process on the training set as depicted in stages 4' and 5'. Most preferably an initial training process is performed in stage 4' wherein feature selection and dimensionality reduction functions are trained to implement the optional dimensionality reduction and feature selection techniques as previously described. Next in stage 5' the classifier is trained and implemented to identify the pain classification of the training set.

Optionally and preferably once the classifier has been trained and set following stage 5' future features obtained from the physiological signals are classified without further training of the classifying system of the present invention and implemented in stages 4 and 5. In stage 4 feature selection and dimensionality reduction is performed according to the dimensionality training determined in stage 4'. Next in stage 5 classifications is performed with a classifier to determine the pain according to the dimensionality reduced GPF vector. Finally in stage 6 pain monitoring and classification is displayed according to the appropriate time scale.

EXAMPLE 1: PAIN CLASSIFICATION UTILIZING A COMBINATION OF FISHER SCORE+SFLDA+REALADABOOST

The following is a non limiting example of the implementation of pain monitoring according to an optional embodiment of an optional method for pain monitoring and classification according to the present invention. The following example provides an illustrative example of pain classification for pain monitoring in a subject wherein the processing methods comprise utilizing a priori data, feature extraction and selection based on Fisher Score rank, dimensionality reduction using SFLDA, and classification using a RealAdaboost classifier within a Boosting framework.

Materials and Methods

An experiment was conducted in order to develop, validate performances and evaluate efficacy of the classification method and system for non-invasive automated pain monitoring according to the present invention. Primary outcome measures was to compare the pain monitoring results with the subjective pain report measured by the visual Numeric Pain Scale (NPS) to a given pain stimulus with reports divided to pain/no-pain (binary test).

The study included 26 healthy volunteers. Inclusion criteria were: (I) free from chronic pain of any type, (II) no medication usage except for oral contraceptives, (III) ability to understand the purpose and instructions of the study, and (IV) blood pressure<140/90. Exclusion criteria were: (I) any type of preexisting condition, (II) use of medications or recreational drugs, or (III) pregnancy. The study was approved by the local ethics committee, and a written informed consent was obtained from all participants prior to the beginning of the experiment.

The cold pressor test (CPT) and heat pain test were chosen to provoke the experimental pain. The cold pressor test apparatus (ChillSafe 8-30, ScanLaf A/S Denmark) is a temperature-controlled water bath with a maximum temperature variance of ±0.5° C., which is continuously stirred by a pump. Volunteers were asked to place their right foot (until above the ankle) in the CPT bath in a still position and maintain their foot in the water for 1 min each session. A thermal testing analyzer (TSA) thermode of 30×30 mm (Medoc TSA-2001 device, Ramat Ishai, Israel) was attached to the skin of the right forearm to initiate heat pain. During pain stimuli sessions the thermode was heated at 10° C./sec to the target temperature (39° -48.5° C.) and with a plateau lasting 60 sec.

In order to evaluate the volunteer's cold and heat pain sensitivity they were exposed to a range of different temperatures and reported perceived pain on a 0-100 numeric pain scale (NPS). For evaluation of subject's heat pain sensitivity they were exposed to 11 heat stimuli, ranging from 37° C. to 50° C. with increasing rate of 10° C./sec, each with a plateau lasting for 10 seconds. In order to evaluate subject's cold pain sensitivity we expose subjects for one min to the CPT using water temperature of 12° C. Subjects reported their pain every 10 sec. The cold and heat apparatus were then appropriately calibrated to initiate feeling of no-pain (NPS 0-30), and pain (NPS>70). Due to the limitations of the GCP and ethics committee approval, the minimum/maximum temperatures used were 1° C. for the cold pain and 48.5° C. for the heat pain.

Subjects received a full explanation about the purpose and design of the study and signed a written informed consent form. Prior to the beginning of the experiment, the familiarizing and calibration sessions were conducted. Next, the experimenter connected the sensors to the subject and during the next 5 min physiological signals were rerecorded for baseline normalization purposes. During the two sessions each participant received 4 heat stimuli and 3 cold stimuli sessions, lasting for 1 minute each with intervals of 10-15 minutes between stimuli and 30-45 minutes between sessions. Volunteers were unaware of the stimuli intensity. The order of the heat pain stimuli was randomly assigned, while the order of the cold stimuli was progressive from low to high level of pain (to avoid adaptation). The "no-pain" stimuli (25° C. CPT and 39° C. heat sensor) was introduced with intention to stimulate a sensory experience similar to pain sessions but without painful stimulus.

The NPS report, the physiological signals and the intensity of stimuli were recorded and synchronized for subsequent processing.

The physiological signals were recorded and stored in a personal computer by the BioPac MP 100 system (BioPac System Inc., Calif., USA) and its companion software AcqKnowledge 3.9.1 (BioPac System Inc.). One-lead electrocardiogram (ECG) signal, 2-channel electroencephalogram (EEG) signal from forehead, photoplethysmograph (PPG) signal from right hand finger, and one lead external electromyogram (EMG) signal from right trapezius muscle were sampled with a frequency of 500 Hz. External skin temperature from the dorsum of the right hand, respiration, and galvanic skin response (GSR) from right hand fingers were sampled with a frequency of 32.5 Hz. In addition, continuous blood pressure signal was non-invasively measured using the Finometer MIDI (Finapres Medical Systems BV, Amsterdam, The Netherlands) and data were recorded using companion software BeatScope EASY (Finapres Medical Systems BV). Continuous blood pressure was sampled with a frequency of 200 Hz.

The recorded physiological signals were extracted, synchronized and processed in off-line way using Matlab® 2009 scientific software (The Mathworks, Inc., Mass., USA).

The data was processed offline on PC computer. All signals were processed using routine signal processing methods for noise and artifact filtering (Oppenhem & Shafer 1999). For some signals (EEG, ECG, etc.) were used signal-specific data processing methods (Rangayyan 2002, Sannei & Chambers 2007). All extracted parameters were averaged (if applicable) with non-overlapping windows of 10 sec. Features utilized are summarized in Table 1 above were extracted from a plurality of raw physiological data. The extracted features were deployed to training and validate classification algorithm.

The machine learning module implemented as described in greater detail in FIG. 2B above.

During the preprocessing and normalization stages the data was manually examined by trained professional. Patients with over-sensitivity and under-sensitivity were removed from training data. This exclusion from training data set is a non-limiting example of a priori knowledge that is incorporated into the system and method of the present invention most preferably to improve classification results. Nevertheless, the data excluded from training the optional classifier was used to test the classifier.

Next, feature normalization was performed by removing the patient's features baseline mean and normalizing the patient's feature baseline variability, in the following manner:

$$\frac{X_i - avg(X_i^{baseline})}{std(X_i^{baseline})}$$

Next Feature Selection step was performed. During the training phase features with maximum Fisher score were selected. Fisher score of i'th feature was defined as $$F_i = \frac{\left(avg(X_j^{pain}) - avg(X_i^{no\text{-}pain})\right)^2}{var(X_i^{pain}) + var(X_i^{no\text{-}pain})}$$

The 100 best features with highest Fisher scores were predetermined during the training phase. During feature selection only the 100 highly ranked features were kept, the remaining features were removed from consideration.

Next, Dimensionality Reduction was performed. During the training phase of the non-limiting and optional method according to the present invention a transformation matrix was determined based on the principle of Sparse Fisher Linear Discriminant Analysis (SFLDA). The methods for calculation of a single SFLDA transformation vector were rigorously described in (Moghaddam, et al., 2006). wherein the transformation vector is calculated either by exhaustive search or using greedy algorithms (forward or backward). Multiplication of the transformation vector by a vector of the selected features following feature selection as described above, results in a number which represents the first reduced discriminate dimension. For pain monitoring unique specification, novel iterative procedure for finding multiple transformation vectors and discriminative components was used as follow:

Input: B—N×N pooled between-class covariance matrix,
W—N×N pooled within-class covariance matrix,
k—required sparsity level for transformation vectors,
P—number of transformation vectors Algorithm:
1. Set p=1, $I^p=\{1 \ldots N\}$
2. Input $B_{I^p}$, $W_{I^p}$ into SFLDA algorithm in order to compute optimum sparsity pattern $I_{opt}^p$ sparse transformation vector $\alpha_{opt}^p$.
3. Set $I^{p+1}=I^p/I_{opt}^p$. Set p=p+1. If p<P go back to step 2.

Output: Set of sparsity patterns $\{I_{opt}^1, \ldots, I_{opt}^P\}$ and transformation matrix $A=[\alpha_{opt}^1 \ldots \alpha_{opt}^P]$.

Transformation matrix A was multiplied by a vector of selected features and transformed it into a new vector most preferably having a significantly reduced dimension. This modification of SFLDA is known as Sparse Linear Discriminant Component Analysis (SLDCA). In an experiment each transformation vector had sparsity level 5, and a total 10 such vectors were computed. Therein according to this non-limiting example a feature set of 100 was reduced to 10 following an optional dimensionality reducing step comprising SFLDA as described above The final stage of classification according to an optional method of the present invention was set to classify the vector of reduced dimensions into a binary class of Pain and No-Pain classes. An optional classifier according to the present invention, RealAdaboost was chosen and trained during a training phase.

In order to assess performances of proposed method and apparatus the leave-one-out cross-validation (Hastie et al., 2009) scheme has been used. In order to prevent the situation where the algorithm was both trained and validated on the same data (in our case same subject), the algorithm was applied N times, where N is the number of subjects. At each run, data were included in the training set from all subjects excluding one, and then the trained algorithm was scored on data from this subject. The Test Error is estimated by averaging over classification errors from each of the N runs.

The algorithm was also tested on patients, which were declared as outliers. In such cases, the algorithm was trained on all non-outlier patients and was tested on all outliers.

Results

The performance of the algorithm is presented in the Table 2. The overall agreement, sensitivity, and positive predictive values (PPV) are presented, together with their respective 95% exact binomial confidence intervals

TABLE 2

Results

|  |  | Pain level estimated | | |
|---|---|---|---|---|
|  |  | pain | no pain | Total |
| Pain level | pain | 425 | 68 | 493 |
|  | no pain | 181 | 1528 | 1709 |
|  | Total | 606 | 1596 |  |

TABLE 3

Pain vs. No pain

|  | Percent | 95% exact binomial confidence interval | |
|---|---|---|---|
| Overall agreement | 88.69% | 87.29% | 89.99% |
| PPV pain | 70.13% | 66.31% | 73.75% |
| PPV no pain | 95.74% | 94.63% | 96.68% |
| Sensitivity pain | 86.21% | 82.84% | 89.13% |
| Sensitivity no pain | 89.41% | 87.85% | 90.83% |

EXAMPLE 2: FEATURE SELECTION AND DIMENSIONALITY REDUCTION

The following example is of a non-limiting example showing the importance of machine learning techniques according to the present invention to improve and provide for pain monitoring, classification and identification. During the clinical study described in Example 1 above all features described in Table 1 were measured. Physiological signals such as an accelerometer, SPO2 were excluded as the clinical study was performed on awake patients. Fisher scores were calculated to rank all available features, according to an optional method of the present invention.

Figure 5A:
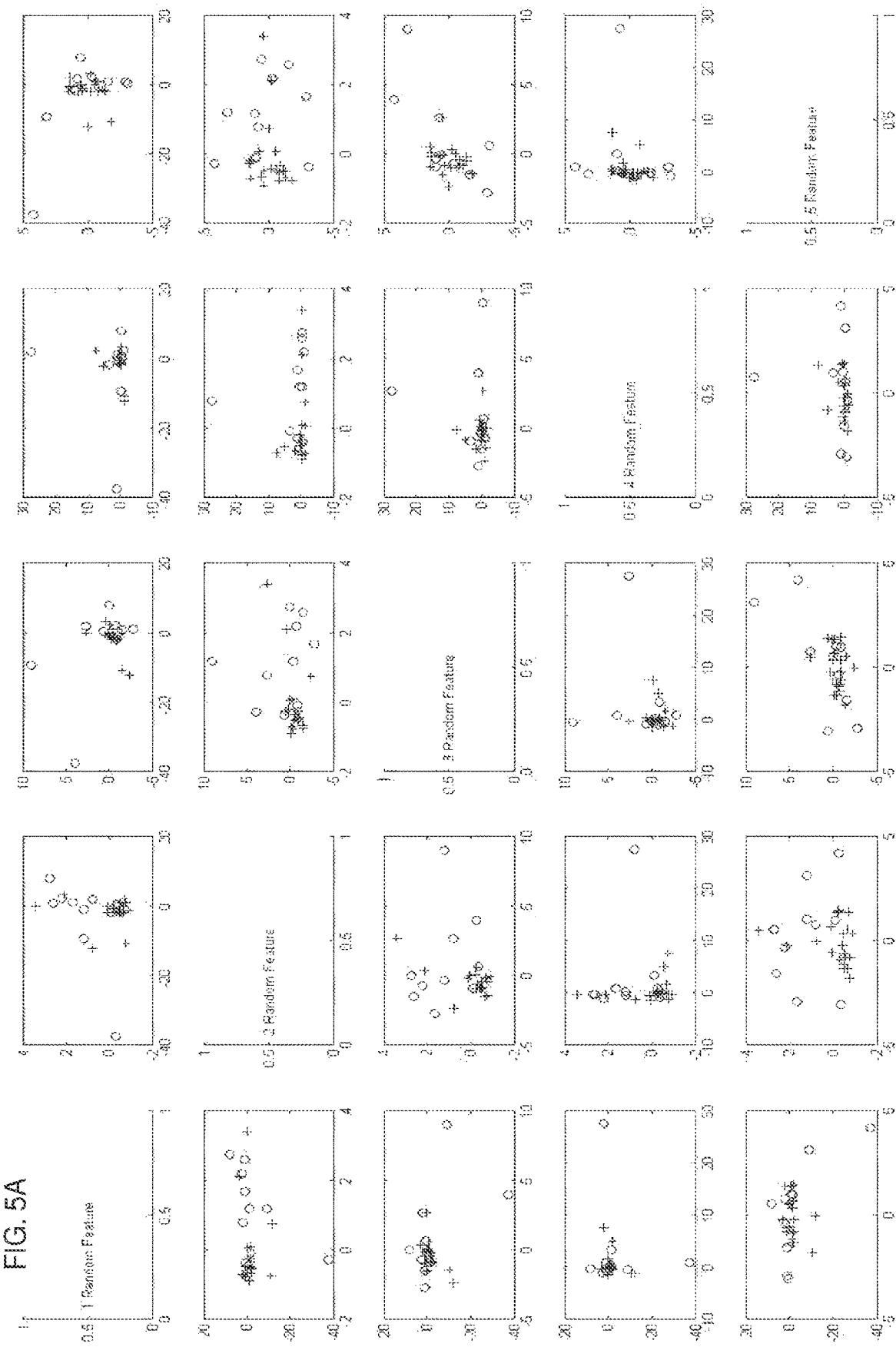
FIGS. 5A-C are scatter plots depicting pain classification according to an optional system and method of the present invention.
Figure 5B:
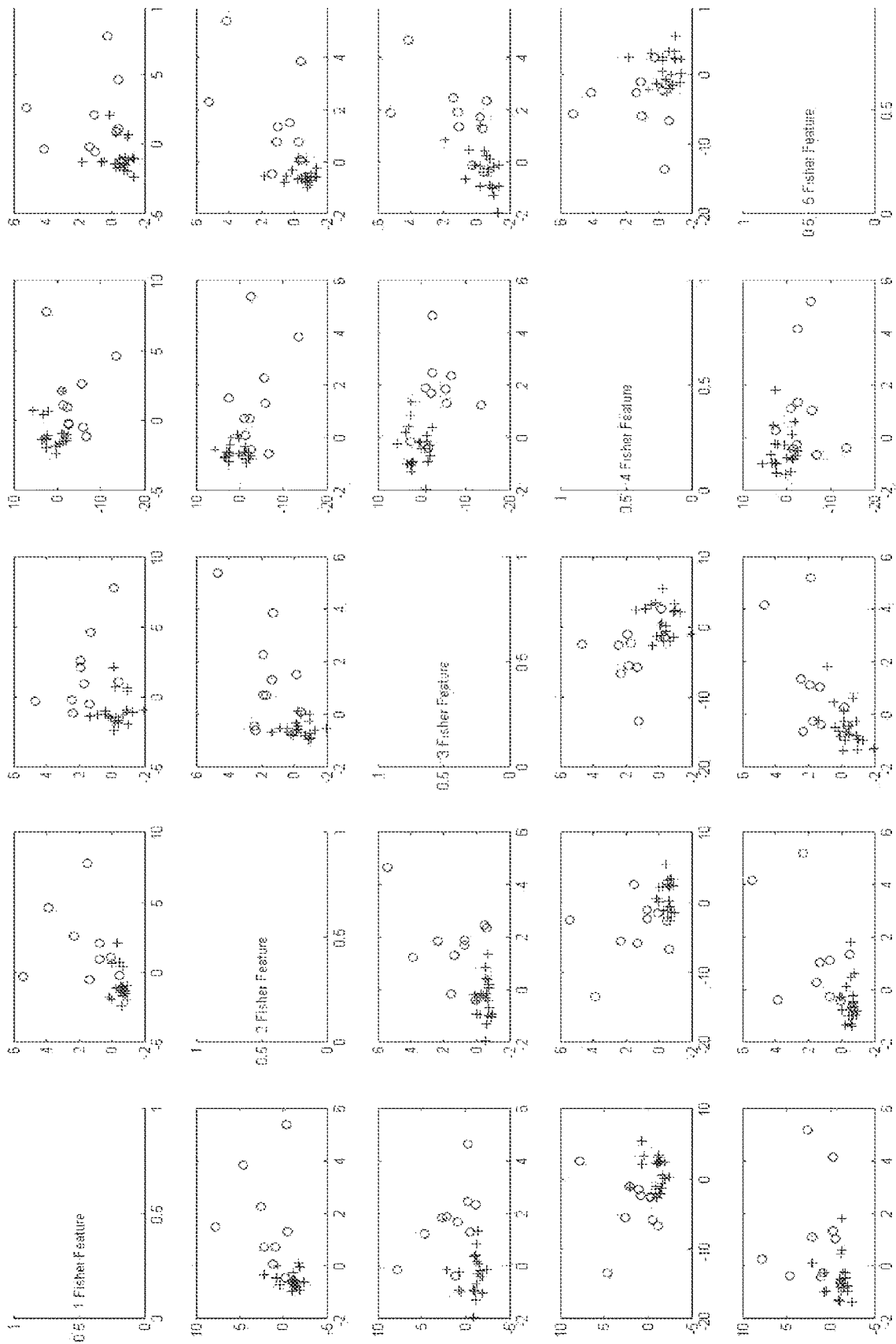
Figure 5C:
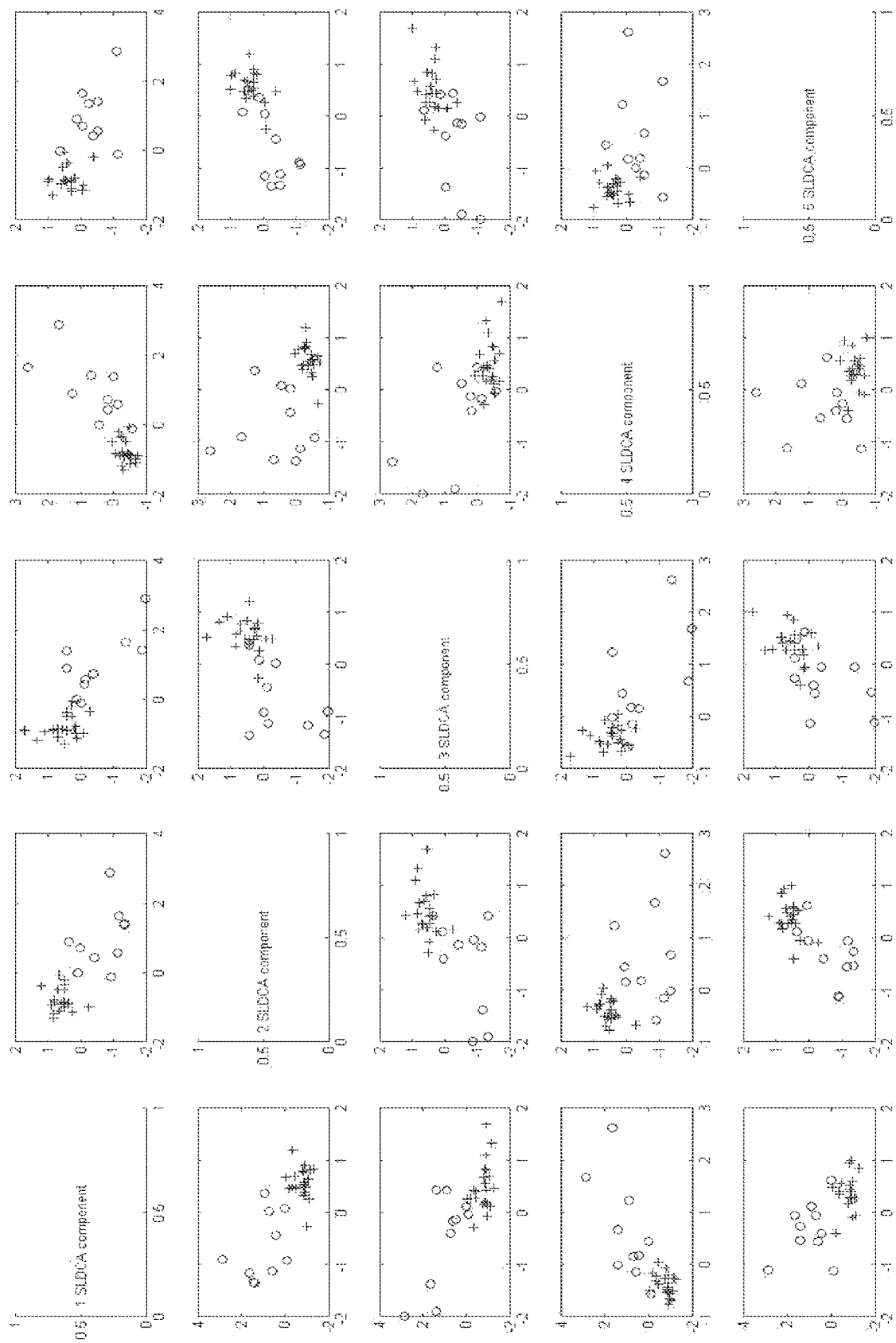

Analysis of the features showing the following features as having a high Fisher score, as summarized in Table 4 and FIGS. 5A-C.

As can be seen these parameters represent both an autonomic system activity of a patient (e.g. amplitudes of PPG signal, Count of Spontaneous Fluctuations in GSR signal, H.R.V extracted from PPG or ECG and its spectral analysis) as well as behavioral activity, such as respiration rate and deviation, muscle activity (which may suggest on a certain discomfort).

TABLE 4

| Signal | Temporal Feature | Spectral Features | Total Features |
|---|---|---|---|
| GSR | Count of Spontaneous Fluctuations (Peaks), Weighed Sum of Peaks (weighted by their amplitude), Signal Max value in window, Smoothed Signal Value in window | Power of frequency bands VLF/LF/HF/above HF | 8 |
| PPG | Mean and Standard Deviation of amplitude of Peak, Trough, and Max Rate point. Mean and Standard Deviation of AUC, Peak to Notch interval, and Pulse Transition Time (Peak to R-ECG interval). | Power of frequency bands HF and LF, and LF/HF ratio calculated from spectral analysis of Peak to Notch interval and Pulse Transition Time. | 9 |
| Respiratory | Mean and Standard Deviation of the amplitude of Peak, Peak to Peak interval (respiratory rate), Smoothed Signal value, Signal Max and Min values in Window | Power of frequency bands VLF/LF/HF/above HF | 9 |
| Temperature | Weighed Sum of Peaks (fluctuations) in window, Mean amplitude of Peaks in window | Power of frequency bands VLF/LF/above HF. | 9 |
| ECG | Mean and Standard Deviation of R peak | Power of HF and LF bands from Heart rate variability | 4 |
| EEG/EMG | Barlow's mean amplitude, Hjorth's mobility, between channels covariance (we use 2-channel EEG), time differentials of a signal. | Energy in band 30-70 Hz, mean power, Barlow's mean frequency and spectral purity | 9 |
| EGG |  | Power of below LF band | 1 |

For example, FIG. 5A depicted scatter plots of 5 random features showing two classes of pain namely pain ("o" open circles and) and non pain ("+" plus sign) for a classification attempted with the initial features that have not undergone dimensionality reduction according to the present invention. Accordingly, inspection of the scatter plots clearly shows that the two classes are not separable either by linearly or non-linearly classification.

FIG. 5B depicts scatter plots of 5 features extracted from the GPF vector based on the highest Fisher scores and as depicted in Table 4:
  1st Fisher feature is (combination): number of Peaks, Weighed Sum of Peaks, Signal Max value in window, Smoothed Signal Value in window of GSR signal.
  2nd Fisher feature is: Power of HF band of GSR signal.
  3rd Fisher feature is: Standard deviation of Peaks to peak intervals of Respiratory signal.
  4th Fisher feature is combination: Mean of Peak, Maximum Rate Point, and Trough Heart Rate from PPG signal.
  5th Fisher feature is: Standard deviation of amplitude of Peaks of Respiratory signal.

Although inspection of FIG. 5B shows that scoring features provides improved classification as can be seen by the reduced overlap between the two classes depicted when compared to FIG. 5A however a substantial degree of overlap is observed.

FIG. 5C depicts scatter plots of 5 SLDCA components wherein dimensionality reduction technique utilized SLDCA substantially improves pain classification between the two classes.

1st SLDCA component comprises a combination of:
Standard deviation of Peaks to peak intervals of Respiratory signal (3 Fisher feature)
Deviation of amplitude of Peaks of Respiratory signal (5 Fisher feature)
Number of Peaks, Weighed Sum of Peaks, Signal Max value in window, Smoothed Signal Value in window of GSR signal (1 Fisher feature)
Power of LF band of PPG signal
Mean of Peak, Maximum Rate Point, and Trough, Heart Rate from PPG signal (4 Fisher feature).
2nd SLDCA component comprises a combination of:
Mean of the amplitude of Peak of Respiratory signal
Standard Deviation of amplitude of Peak of Respiratory signal
Power of bellow LF band EGG
Between channels covariance EEG
Power of above HF band of GSR
3rd SLDCA component is a combination of:
First differential of EMG signal
Standard Deviation of Peak-to-Peak interval of EGG
Peak-to-Notch interval of PPG.
Power of HF band of peak-to-notch variability.
Power of VLF band Temperature
4th SLDCA component is a combination of:
Power of HF band of Respiratory signal.
Heart Rate from ECG signal
Standard Deviation of amplitude of Peak of EGG
Pulse transition time (Peak to R) from ECG and PPG
Standard Deviation of Peak-to-Notch interval of PPG
5th SLDCA component is a combination of:
Power of bellow VLF band of Respiratory
Power of LF band EGG
Standard Deviation of Pulse transition time (Peak to R) from ECG and PPG
LF/HF ratio of PPG
Power of LF band Temperature Although inspection of FIG. 5C shows that SLDCA dimensionality reduction provides improved classification as can be seen by the reduced overlap between the two classes depicted when compared to FIG. 5B still a substantial degree of overlap is observed, therefore classification module is still required.

EXAMPLE 3: PAIN CLASSIFICATION UTILIZING A COMBINATION OF HIERARCHICAL DIMENSIONALITY REDUCTION+RANDOM FOREST CLASSIFICATION

The following example is of a non-limiting example showing the importance of machine learning techniques according to the present invention to improve and provide for pain monitoring, classification and identification, as depicted in FIG. 2C wherein the system and method of the present invention comprises a wherein feature selection and dimensionality reduction is provided by Hierarchical Dimensionality Reduction (HDR), and classification is provided by a Random Forest classifier.

Subjects

The study included 36 healthy volunteers, 23 female and 13 male, aged 20 to 38 years (mean (SD) 26(4.3)). Inclusion criteria were: (I) free from chronic pain of any type, (II) no medication usage except for oral contraceptives, (III) ability to understand the purpose and instructions of the study, and (IV) blood pressure<140/90. Exclusion criteria were: (I) any type of preexisting condition, (II) use of medications or recreational drugs, or (III) pregnancy. The study was approved by the local ethics committee, and a written informed consent was obtained from all participants prior to the beginning of the experiment.

Instruments for Pain and Stress Stimulation

Assessment of Cold and Heat Pain Perception

The cold pressor test (CPT) and heat pain test were chosen to provoke the experimental pain. The cold pressor test apparatus (ChillSafe 8-30, ScanLaf A/S Denmark) is a temperature-controlled water bath with a maximum temperature variance of ±0.5° C., which is continuously stirred by a pump. Volunteers were asked to place their right foot (until above the ankle) in the CPT bath in a still position and maintain their foot in the water for 1 min each session. A thermal testing analyzer (TSA) thermode of 30×30 mm (Medoc TSA-2001 device, Ramat Ishai, Israel) was attached to the skin of the right forearm to initiate heat pain.

During pain stimuli sessions the thermode was heated at 10° C./sec to the target temperature (39°-48.5° C.) and with a plateau lasting 60 sec.

In order to evaluate the volunteer's cold and heat pain sensitivity they were exposed to a range of different temperatures and reported perceived pain on a 0-100 numeric pain scale (NPS). For evaluation of subject's heat pain sensitivity they were exposed to 11 heat stimuli, ranging from 37° C. to 50° C. with increasing rate of 10° C./sec, each with a plateau lasting for 10 seconds. In order to evaluate subject's cold pain sensitivity we expose subjects for one min to the CPT using water temperature of 12° C. Subjects reported their pain every 10 sec. The cold and heat apparatus were then appropriately calibrated to initiate feeling of no-pain (NPS 0-15), mild pain (NPS 15-45), moderate pain (NPS 45-75), and severe pain (NPS>75). Due to the limitations of the GCP and ethics committee approval, the minimum/maximum temperatures used were 1° C. for the cold pain and 48.5° C. for the heat pain. On several occurrences the calibrated temperatures of "moderate pain" were significantly close to minimum/maximum allowed temperatures. At such cases "severe pain" stimuli temperatures were set to minimum/maximum temperatures.

Mental Stress Protocol

The control sessions of mental stress was performed. In order to induce mental stress the mental arithmetic test Paced Auditory Serial Addition Task (PASAT), (Gronwall & Wrightson 1974) has been used, which consists of 1 min of auditory presentation of random digits from one to nine, with an interval of 2 sec. The subjects' were asked continuously express the sum of the two last digits.

Physiological Signals Recording

The physiological signals were recorded and stored in a personal computer by the BioPac MP 100 system (BioPac System Inc., Calif., USA) and its companion software AcqKnowledge 3.9.1 (BioPac System Inc.). One-lead electrocardiogram (ECG) signal, 2-channel electroencephalogram (EEG) signal from forehead, photoplethysmograph (PPG) signal from right hand finger, and one lead external electromyogram (EMG) signal from right trapezius muscle were sampled with a frequency of 500 Hz. External skin temperature from the dorsum of the right hand, respiration, and galvanic skin response (GSR) from right hand fingers were sampled with a frequency of 32.5 Hz. In addition, continuous blood pressure signal was non-invasively measured using the Finometer MIDI (Finapres Medical Systems BV, Amsterdam, The Netherlands) and data were recorded using companion software BeatScope EASY (Finapres Medical Systems BV). Continuous blood pressure was sampled with a frequency of 200 Hz.

Data Processing and Parameters Extraction

The recorded physiological signals were extracted, synchronized and processed in off-line way using Matlab® 2009 scientific software (The Mathworks, Inc., Mass., USA).

All signals were processed using routine signal processing methods for noise and artifact filtering (Oppenhem & Shafer 1999). For some signals (EEG, ECG, etc.) were used signal-specific data processing methods (Rangayyan 2002, Sannei & Chambers 2007). All extracted parameters were averaged (if applicable) with non-overlapping windows of 10 sec. The detailed list of parameters which were extracted from above mentioned physiological signals can be found in Table 1

Normalization and Averaging

All continuous parameters were normalized by removing the parameter's baseline mean and normalizing the parameter's baseline variability, in the following manner:

$$\frac{X_i - avg(X_i^{baseline})}{std(X_i^{baseline})}$$

In order to avoid bias and over-fitting, baseline signals of a specific subject was not used for normalization of the subject's parameters. In other words parameters of the subject where normalized based on baseline parameters of all other volunteers. Categorical parameters were not normalized.

Finally, the parameters during each stimulus were averaged. Thus each 1 min stimulus was represented by a vector of normalized parameters extracted from recorded physiological signals.

Dimensionality Reduction

All parameters with correlation r>0.8 were identified and consequently averaged by Hierarchical Dimensionality Reduction (HDR) method Duda et al. 2000.

Classification Algorithm: Random Forest

The goal of the presented example was to demonstrate abilities of a pain monitoring device which optionally and preferably provides for predicting the presence of pain sensation and classify its level. A first vector, according to optional embodiments of the present invention, comprising temporal, spectral, and other parameters extracted during data processing and parameter extraction step constitutes prediction variables which we will use in prediction procedure.

In this example the classification algorithm which has been chosen was the Random Forest. Random Forest (Breiman 2001b) is a statistical learning procedure that makes a prediction by aggregating the results from an ensemble of classification and regression trees (CART) (Breiman et al. 1984). Random Forest averages over multiple CART trees increase the stability of the final algorithm. Each tree is grown on a bootstrapped sample (random sampling with repetition) of original training data. During the growing process of each tree, features are randomly sampled as well to find a best split of each node of the tree.

Classification Algorithm Testing Methodology

In order to assess performances of proposed method and apparatus the leave-one-out cross-validation (Hastie et al., 2009) scheme has been used. In order to prevent the situation where the algorithm was both trained and validated on the same data (in our case same subject), the algorithm was applied N times, where N is the number of subjects. At each run, data were included in the training set from all subjects excluding one, and then the trained algorithm was scored on data from this subject. The Test Error is estimated by averaging over classification errors from each of the N runs.

Study Design

Subjects received a full explanation about the purpose and design of the study and signed a written informed consent form. Prior to the beginning of the experiment, the familiarizing and calibration sessions were conducted. Next, the experimenter connected the sensors to the subject and during the next 5 min physiological signals were rerecorded for baseline normalization purposes. After the baseline the physical stress session was performed. During the two sessions each participant received 3 heat stimuli and 3 cold stimuli sessions (mild pain, moderate pain and severe pain), lasting for 1 minute each with intervals of 10-15 minutes between stimuli and 30-45 minutes between sessions. Volunteers were unaware of the stimuli intensity. The order of the heat pain stimuli was randomly assigned, while the order of the cold stimuli was progressive from low to high level of pain (to avoid adaptation). The "no-pain" stimuli (25° C. CPT and 39° C. heat sensor) was introduced with intention to stimulate a sensory experience similar to pain sessions but without painful stimulus.

Results

The performance of the algorithm is assessed by presenting tables of the stimuli inflicted on the volunteers by experimenter versus the pain as predicted and classified by the classification software based solely on recorded physiological signals.

Since the cost function was used in the training of the classification algorithm, the weight matrices should be used to rank the estimation error, i.e., to give a smaller penalty to a small error than a large one; for example, in case of high pain stimulation, the device estimation of "no pain" will be considered a worse error than a "mild pain" estimation. If pain levels are ranked by their severity (increasing or decreasing order) the "weight" of estimated pain level i given stimulated pain level j are defined according to the formula:

$$w(i,j)=1-abs(i-j)/(N-1),$$

where N is a total number of pain levels, and abs( ) denotes absolute value. This formula intends to introduce ranking constraint into pain level estimation.

The weighting matrix used in the case of three categories is:

|  | Pain level estimated | | |
| --- | --- | --- | --- |
| Pain level stimulated | Severe | Mild | No Pain |
| Severe | 1 | 1/2 | 0 |
| Mild | ½ | 1 | 1/2 |
| No Pain | 0 | 1/2 | 1 |

In case of two categories no weights are used, in other words all errors had equal costs. In these cases the overall agreement, sensitivity, and positive predictive values (PPV) are presented, together with their respective 95% exact binomial confidence intervals. Weights are introduced in sensitivity and PPV calculations for multiclass cases. Thus, the resulted sensitivity and PPV values along with their corresponded CI values are weighted sensitivity, PPV and CI respectively. In these cases, the weighted overall agreement, weighted sensitivity and weighted PPV are presented, together with their respective 95% exact Wilson-score confidence intervals.

TABLE 5

Severe pain vs. No pain

|  |  | Pain level estimated | | |
| --- | --- | --- | --- | --- |
|  |  | severe pain | no pain | Total |
| Pain level inflicted | severe pain | 249 | 33 | 282 |
|  | no pain | 28 | 271 | 299 |
|  | Total | 277 | 304 | 581 |

TABLE 6

Severe pain vs. No pain

|  | Percent | 95% exact binomial confidence interval | |
| --- | --- | --- | --- |
| Overall agreement | 89.50% | 86.72% | 91.87% |
| PPV severe pain | 89.89% | 85.72% | 93.18% |
| PPV no pain | 89.14% | 85.09% | 92.41% |
| Sensitivity severe pain | 88.30% | 83.96% | 91.81% |
| Sensitivity no pain | 90.64% | 86.75% | 93.69% |

TABLE 7

Severe pain vs. Mental Stress

|  |  | Pain level estimated | | |
| --- | --- | --- | --- | --- |
|  |  | severe pain | mental stress | Total |
| Pain level inflicted | severe pain | 292 | 37 | 329 |
|  | mental stress | 69 | 260 | 329 |
|  | Total | 361 | 297 | 658 |

TABLE 8

Severe pain vs. Mental Stress

|  | Percent | 95% exact binomial confidence interval | |
| --- | --- | --- | --- |
| Overall agreement | 83.89% | 80.85% | 86.62% |
| PPV severe pain | 80.89% | 76.44% | 84.81% |
| PPV mental stress | 87.54% | 83.24% | 91.07% |
| Sensitivity severe pain | 88.75% | 84.83% | 91.96% |
| Sensitivity mental stress | 79.03% | 74.22% | 83.30% |

TABLE 9

Severe pain vs. Mild Pain vs. No pain

|  |  | Pain level estimated | | | |
| --- | --- | --- | --- | --- | --- |
|  |  | severe pain | mild pain | no pain | Total |
| Pain level inflicted | severe pain | 191 | 75 | 16 | 282 |
|  | mild pain | 59 | 178 | 39 | 276 |
|  | no pain | 4 | 69 | 226 | 299 |
|  | Total | 254 | 322 | 281 | 857 |

TABLE 10

Severe pain vs. Mild Pain vs. No pain

|  | Percent | 95% exact Wilson confidence interval | |
| --- | --- | --- | --- |
| Overall agreement | 83.55% | 80.92% | 85.88% |
| PPV severe pain | 86.81% | 82.10% | 90.43% |
| PPV mild pain | 77.64% | 72.78% | 81.85% |
| PPV no pain | 87.37% | 82.97% | 90.75% |
| Sensitivity severe pain | 81.03% | 76.05% | 85.18% |
| Sensitivity mild pain | 82.25% | 77.30% | 86.30% |
| Sensitivity no pain | 87.12% | 82.85% | 90.45% |

These results show that the system and method implemented according to the present invention is capable of classifying and detecting the pain status in a patient as shown in Tables 6, 8 and 10

REFERENCES

Akselrod, S., D. Gordon, F. A. Ubel, D. C. Shannon, A. C. Berger, and R. J. Cohen. "Power spectrum analysis of heart rate fluctuation: a quantitative probe of beat-to-beat cardiovascular control." *Science* 213, no. 4504 (July 1981): 220-222.

Belkin, M., and P. Niyogi. "Laplacian eigenmaps for dimensionality reduction and data representation." *Neural Computation* 15 (2003): 13731396.

Bishop, C. M. *Pattern recognition and machine learning.* New York: Springer, 2006.

Borg, I., and P. Groenen. *Modern Multidimensional Scaling: theory and applications.* New York: Springer-Verlag, 2005.

Breiman L, Friedman J, Olshen R, Stone C. Classification and Regression Trees. Belmont, Calif.: Wadsworth; 1984.

Breiman, L, "Bagging Predictors." *Machine Learning* 24, no. 2 (1996): 123-140.

Breiman, L. "Random Forests." *Machine Learning* V45, no. 1 (October 2001): 5-32.

Breiman L. Random Forests, Machine Learning J., 2001b; 45:5-32.

Bruhn, J., H. Ropcke, and A. Hoeft. "Approximate entropy as an electroencephalographic measure of anesthetic drug effect during desflurane anesthesia." *Anesthesiology* 92, no. 3 (March 2000): 715-726.

Chapelle, O., V. Vapnik, O. Bousquet, and S. Mukherjee. "Choosing Kernel Parameters for Support Vector Machines." *Machine Learning*, 2000

Cohen, D. H., and S. M. Sherman. "The autonomic nervous system and its central control." Edited by R. Berne, and M. Levy, 322. St. Louis: C. V. Mosby, 1983.

Coifman, R. R., et al. "Geometric diffusions as a tool for harmonic analysis and structure definition of data." *Proceedings of the National Academy of Sciences* 102 (2005): 7426-7438.

d'Aspremont, A., L. El Ghaoui, M. I. Jordan, and G. R. G. Lanckriet. "A direct formulation for sparse PCA using semidefinite programming." Cambridge, Mass.: MIT Press, 2005.

Deschamps, A., I. Kaufman, S. B. Backman, and G. Plourde. "Autonomic nervous system response to epidural analgesia in laboring patients by wavelet transform of heart rate and blood pressure variability." *Anesthesiology* 101, no. 1 (July 2004): 21-27.

Duda R, Hart P, Stork D. Pattern Classification. New York: Willey; 2000.

Donoho, D. L., and C. Grimes. "Hessian eigenmaps: Locally linear embedding techniques for high-dimensional data." *PNAS* 100, no. 10 (May 2003): 5591-5596.

Goncharova, I. I., and J. S. Barlow. "Changes in EEG mean frequency and spectral purity during spontaneous alpha blocking." *Electroencephalography and clinical neurophysiology* 76, no. 3 (September 1990): 197-204.

Gronwall D, Wrightson P. Delayed Recovery of intellectual function after minor head injury. *Lancet* 2 (1974):605-609.

Guignard, B. "Monitoring analgesia." *Best practice and research. Clinical anaesthesiology* 20, no. 1 (March 2006): 161-180.

Guo, Y., T. Hastie, and R. Tibshirani. "Regularized linear discriminant analysis and its application in microarrays." *Biostatistics* (Oxford University Press) 8, no. 1 (January 2007): 86-100.

Guyton, A. C. *Human Physiology and Mechanisms of Disease*. Philadelphia: Saunders, 1982.

Fagrell, B. *Microcirculation of the skin. The physiology and pharmacology of the microcirculation*. Vol. 2. New York: Academic Press, 1984.

Hastie, T., R. Tibshirani, and J. Friedman. *The elements of statistical learning: data mining, inference, and prediction.* New York: Springer, 2009.

Hjorth, B. "The physical significance of time domain descriptors in EEG analysis." *Electroencephalography and clinical neurophysiology* 34, no. 3 (March 1973): 321-325.

Kohavi, R., and G. H. John. "Wrappers for Feature Subset Selection." *Artificial Intelligence* 97, no. 1-2 (1997): 273324.

Lidberg, L., and G. B. Wallin. "Sympathetic Skin Nerve Discharges in Relation to Amplitude of Skin Resistance Responses." *Psychophysiology* 18, no. 3 (1981): 268-270.

Malik, M. "Heart rate variability: standards of measurement, physiological interpretation and clinical use. Task Force of the European Society of Cardiology and the North American Society of Pacing and Electrophysiology." *Circulation* 93, no. 5 (March 1996): 1043-1065.

Moghaddam, B., Y. Weiss, and S. Avidan. "Spectral Bounds for Sparse PCA: Exact and Greedy Algorithms." Edited by Weiss, Y., Scholkopf, B. and Platt, J., 915-922. Cambridge, Mass.: MIT Press, 2006.

Moghaddam, B., Y. Weiss, and S. Avidan. "Generalized Spectral Bounds for Sparse LDA." *ICML*. 2006a. 641-648.

Oppenheim A V, Schafer R W. Discrete-time signal Processing. Upper Saddle River, N.J.: Prentice Hall; 1999.

Pagani, M., O. Rimoldi, and A. Malliani. "Low-frequency components of cardiovascular variabilities as markers of sympathetic modulation." *Trends in pharmacological sciences* 13, no. 2 (February 1992): 50-54.

Pan, J., and W. J. Tompkins. "A real-time QRS detection algorithm." *IEEE Trans Biomed Eng* 32, no. 3 (March 1985): 230-236.

Pop-Jordanova, N., and J. Pop-Jordanov. "Spectrum-weighted EEG frequency ("brain-rate") as a quantitative indicator of mental arousal." *Prilozi Makedonska akademija na naukite i umetnostite, Oddelenie za biolovski i medicinski nauki* 26, no. 2 (December 2005): 35-42.

Rangayyan R M. Biomedical signal analysis: A case study approach. IEEE Press, 2002.

Sanei S, Chambers J A. EEG signal processing. New York: John Wiley & Sons; 2007.

Schlogl, Alois. "A comparison of multivariate autoregressive estimators." *Signal Process.* (Elsevier North-Holland, Inc.) 86, no. 9 (September 2006): 2426-2429

Scholkopf, B., A. Smola, and K.-R. Muller. "Nonlinear component analysis as a kernel eigenvalue problem." *Neural Comput.* (MIT Press) 10, no. 5 (1998): 1299-1319.

Seitsonen, E. R., I. K. Korhonen, M. J. Van Gils, J. M. Lotjonen, K. T. Kortilla, and A. M. Yli-Hankala. "EEG spectral entropy, heart rate, photoplethysmography and motor responses to skin incision during sevoflurane anaesthesia." *Acta Anaesthesiol Scand*, 49, (2005): 284292.

Roweis, S., and L. Saul. "Nonlinear dimensionality reduction by locally linear embedding." *Science* 290. (2000): 2323-2326.

Tenenbaum, J., V. de Silva, and J. C. Langford. "A global geometric framework for nonlinear dimensionality reduction." *Science* 290 (2000): 23192323.

Thomas, D. W., and J. M. Evans. "Lower oesophageal contractility monitoring during anaesthesia for cardiac surgery: preliminary observations." *Annals of the Royal College of Surgeons of England* 71, no. 5 (September 1989): 311-315.

Tibshirani, R., T. Hastie, B. Narasimhan, and G. Chu. "Diagnosis of multiple cancer types by shrunken centroids of gene expression." *PNAS* 99, no. 10 (May 2002): 6567-6572.

van den Berg, A. A., D. Savva, and N. M. Honjol. "Attenuation of the haemodynamic responses to noxious stimuli in patients undergoing cataract surgery. A comparison of magnesium sulphate, esmolol, lignocaine, nitroglycerine and placebo given i.v. with induction of anaesthesia." *European Journal of Anaesthesiology* 14, no. 02 (2006): 134-147.

Vapnik, V. N. *Statistical Learning Theory*. Edited by Haykin S. New York: Wiley, 1998.

Wackermann, J. "Towards a quantitative characterisation of functional states of the brain: from the non-linear methodology to the global linear description." *International Journal of Psychophysiology* 34, no. 1 (October 1999): 65-80.

Weiss, T., A. Del Bo, N. Reichek, and K. Engelman. "Pulse transit time in the analysis of autonomic nervous system effects on the cardiovascular system." *Psychophysiology* 17, no. 2 (March 1980): 202-207.

Zou, H., T. Hastie, and R. Tibshirani. "Sparse Principal Component Analysis." *Journal of Computational Graphical Statistics* 15 (2006): 265286.

While the invention has been described with respect to a limited number of embodiments, it will be appreciated that many variations, modifications and other applications of the invention may be made.

What is claimed is:

1. A method for monitoring pain of a patient, the method comprising:
    obtaining at least two physiological signals comprising electrocardiogram (ECG) and at least one signal selected from the group consisting of: Photoplethysmograph (PPG), Galvanic Skin Response (GSR), Blood pressure, respiration, internal body temperature, skin temperature, electrooculography (EOG), pupil diameter, electroencephalogram (EEG), frontalis electromyogram (FEMG), electromyography (EMG), electro-gastro-gram (EGG), partial pressure of carbon dioxide, and accelerometer readings;
    processing said at least two physiological signals to improve signal quality, thereby obtaining at least two processed signals;
    generating a first vector, said first vector comprising at least three features extracted from said at least two physiological signals, wherein said at least three features comprise at least one feature selected from the group consisting of: RR/PQ/PR/QT/RS/ST interval, RR/PQ/PR/QT/RS/ST interval variability, Q/R/S/T/P amplitude, and any combination thereof;
    transforming said first vector into a second vector, said transformation comprising normalization; and
    monitoring the pain status of the patient by applying a classification algorithm adapted to classify said second vector into a graduated scale representing the level of pain;
    wherein said classification algorithm comprises an ensemble of classification and regression trees.

* * * * *